United States Patent
Hanley

(10) Patent No.: US 12,104,298 B2
(45) Date of Patent: Oct. 1, 2024

(54) CURLED FIBER MATS AND METHODS OF MAKING AND USING SAME

(71) Applicant: Resolute FP Canada, Inc., Montreal (CA)

(72) Inventor: Shaune John Hanley, Montreal (CA)

(73) Assignee: Resolute FP Canada, Inc., Montreal (CA)

( * ) Notice: Subject to any disclaimer, the term of this patent is extended or adjusted under 35 U.S.C. 154(b) by 393 days.

(21) Appl. No.: 17/442,780

(22) PCT Filed: Mar. 26, 2020

(86) PCT No.: PCT/US2020/024832
§ 371 (c)(1),
(2) Date: Sep. 24, 2021

(87) PCT Pub. No.: WO2020/198417
PCT Pub. Date: Oct. 1, 2020

(65) Prior Publication Data
US 2022/0170192 A1    Jun. 2, 2022

Related U.S. Application Data

(60) Provisional application No. 62/824,055, filed on Mar. 26, 2019.

(51) Int. Cl.
*D04H 1/06* (2012.01)
*A61F 13/15* (2006.01)
*D21H 15/04* (2006.01)

(52) U.S. Cl.
CPC .............. *D04H 1/06* (2013.01); *D21H 15/04* (2013.01); *A61F 13/15626* (2013.01); *D10B 2201/01* (2013.01); *D10B 2509/026* (2013.01)

(58) Field of Classification Search
CPC ........ D21H 15/04; D21H 17/14; D21H 25/06; D04H 1/06; A61F 13/15626; A61F 13/537; D10B 2201/01; D10B 2509/026
See application file for complete search history.

(56) References Cited

U.S. PATENT DOCUMENTS 5,858,021 A    1/1999  Sun et al.
7,018,508 B2 *  3/2006  Yancey ................. D21C 9/185
                                          162/100

(Continued)

FOREIGN PATENT DOCUMENTS

EP    0429112 A2    5/1991
EP    3988713 B1 * 11/2023  ............. B05C 1/083

(Continued)

OTHER PUBLICATIONS

Supplementary European Search Report and Opinion for corresponding European Application No. 20776962.1 mailed Nov. 2, 2021.

(Continued)

*Primary Examiner* — Jose A Fortuna
(74) *Attorney, Agent, or Firm* — Troutman Pepper Hamilton Sanders LLP; James E. Schutz; Chris N. Davis

(57) ABSTRACT

Disclosed herein are The invention relates to curled fiber mats. The invention further includes methods of making curled fiber mats, comprising forming a fibrous media from a fibrous material, treating the fibrous media with a crosslinking agent to form a treated fibrous media, and drying and/or curing the treated fibrous media to produce a curled fiber mat that has a permanent curl.

19 Claims, 8 Drawing Sheets

(56) References Cited

U.S. PATENT DOCUMENTS

| | | | |
|---|---|---|---|
| 10,266,989 B2* | 4/2019 | Hanley | D21C 9/002 |
| 11,833,018 B2* | 12/2023 | Dalal | A61F 13/49011 |
| 2003/0070776 A1* | 4/2003 | Crow | D21C 9/004 |
| | | | 162/13 |
| 2003/0108739 A1 | 6/2003 | Sun et al. | |
| 2004/0074616 A1 | 4/2004 | Sears et al. | |
| 2009/0199349 A1 | 8/2009 | Weinstein | |
| 2012/0006741 A1 | 1/2012 | Schmidt | |
| 2016/0289895 A1* | 10/2016 | Hanley | D21C 9/005 |
| 2017/0145632 A1 | 5/2017 | Nonni et al. | |
| 2022/0161170 A1* | 5/2022 | Hanley | B01D 39/12 |
| 2022/0170192 A1* | 6/2022 | Hanley | D21H 25/06 |
| 2023/0181377 A1* | 6/2023 | Kasparkova | A61L 15/26 |
| | | | 424/430 |
| 2023/0250586 A1* | 8/2023 | Colman | D21F 11/04 |
| | | | 162/129 |

FOREIGN PATENT DOCUMENTS

| | | | | |
|---|---|---|---|---|
| JP | 10212690 A * | 8/1998 | | D21H 15/04 |
| JP | 7247094 B2 * | 3/2023 | | A61F 13/53 |
| WO | 93/14264 A1 | 7/1993 | | |
| WO | WO-2020198417 A3 * | 6/2021 | | A61F 13/537 |

OTHER PUBLICATIONS

Search Report and Written Opinion for corresponding International Application No. PCT/US2020/024832, mailed Apr. 27, 2021.

* cited by examiner

CURLED FIBER MATS AND METHODS OF MAKING AND USING SAME

CROSS-REFERENCE TO RELATED APPLICATIONS

This application is a U.S. National Phase of International Patent Application No. PCT/US2020/024832, filed on Mar. 26, 2020, which claims priority to U.S. Provisional Application Ser. No. 62/824,055 filed Mar. 26, 2019. The entire contents of these applications are incorporated herein by reference in their entirety.

TECHNICAL FIELD

The present disclosure relates generally to fibrous materials in fibrous media, and methods of making and using the same.

BACKGROUND

Disposable absorbent articles (including, but not limited to, diapers) can include an acquisition and distribution layer interposed between a topsheet and an absorbent core. Various strategies have been employed to help disposable absorbent articles and their acquisition and distribution layers to handle multiple liquid insults. Nonetheless, improved disposable absorbent articles and improved acquisition and distribution layers, and methods of making the same, are desired.

SUMMARY

Disclosed herein are methods comprising forming a fibrous media from a fibrous material, treating the fibrous media with a crosslinking agent to form a treated fibrous media, and drying and/or curing the treated fibrous media to produce a curled fiber mat. In some embodiments, the fibrous material comprises a cellulosic pulp fiber. In some embodiments, the fibrous material comprises Kraft pulp. In some embodiments, the crosslinking agent provides a curled fiber mat with a curl that is very long-lasting and can be permanent.

In some embodiments, the drying is at a temperature of 100° C. or greater. In some embodiments, the drying is for a time from 10 seconds to 90 seconds. In some embodiments, the curing is at a temperature of 145° C. or greater. In some embodiments, the curing is at a temperature of 180° C. to 190° C. In some embodiments, the curing is for a time from 30 seconds or greater. In some embodiments, the curing is for a time from 30 seconds to 120 seconds. In some embodiments, the curing is for a time from 30 seconds to 6 minutes, such as from 1 minute to 5 minutes or from 1.5 minutes to 2 minutes.

In some embodiments, the drying occurs before and separate from the curing. In some embodiments, the curing and the drying occur simultaneously. In some embodiments, the crosslinking agent comprises a carboxylic acid. In some embodiments, the crosslinking agent is selected from the group consisting of citric acid and glutaraldehyde. In some embodiments, the crosslinking agent is present in an amount of 5% to 20% and can be applied to more than one side of the fibrous material, based on the weight of the fibrous material. In some embodiments, the crosslinking agent comprises 3.5% to 5% citric acid, by weight of the fibrous material, and 1% to 2.5% glutaraldehyde, by weight of the fibrous material.

In some embodiments, the curled fiber mat has a final curl index of 0.28 or greater. In some embodiments, the curled fiber mat has a final curl index of 0.32 or greater. In some embodiments, the curled fiber mat has a thickness of 1 mm to 3 mm. In some embodiments, the curled fiber mat has a thickness of 8 mm to 12 mm.

Also disclosed herein are products made by the disclosed methods. In some embodiments, the product is an acquisition and distribution layer. In some embodiments, the product comprises an acquisition and distribution layer. In some embodiments, the product comprises an acquisition and distribution layer and absorbent core. In some embodiments, the curled fiber mat functions as both the acquisition and distribution layer and absorbent core of a hygiene product. In some embodiments, the curled fiber mat comprises curled fibers to a depth of 25% or less. In some embodiments, the curled fiber mat comprises curled fibers to a depth of 10% or less. In some embodiments, the curled fiber mat comprises permanently curled fibers. In some embodiments, the curled fiber mat comprises curled fibers to a depth of greater than 25%. In some embodiments, the curled fiber mat is a curled fiber airlaid mat, e.g., it is produced by an airlaid process. In some embodiments, the curled fiber mat is a curled fiber wetlaid mat, e.g., it is produced by a wetlaid process.

These and other objects, features and advantages of the present invention will become more apparent upon reading the following specification in conjunction with the accompanying description, claims and drawings.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

Figure 1A:
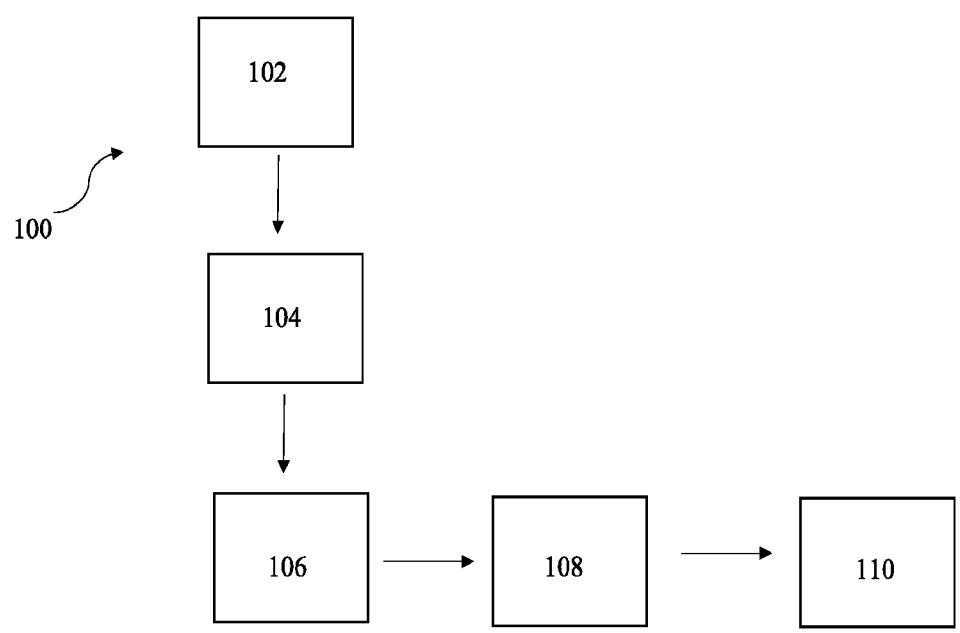
FIGS. 1a-1b illustrate flow charts of the process in accordance with some embodiments of the disclosure.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or," it may mean "exclusive-or," it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, the term "about" should be construed to refer to both of the numbers specified as the endpoint (s) of any range. Any reference to a range should be considered as providing support for any subset within that range. Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

The disclosure describes a curled fiber mat and methods of making and using the same. The process steps for making a curled fiber mat can be represented graphically as a series of steps. For example, FIG. 1a depicts one embodiment for the present disclosure, which discloses process 100 for producing a curled fiber mat. FIG. 1a depicts a process including, but not limited to, providing fibrous material at 102, forming a fibrous media at 104, chemically treating the fibrous media at 106 to form a treated fibrous media, subjecting the treated fibrous media to further processing (e.g., drying and/or curing) at 108 to produce a curled fiber mat 110. The fibrous media can be produced by any method known in the art, including but not limited to needling, hydroentangling, adhesive bonding, spray bonding, thermal bonding, calendar bonding, through-air bonding, infrared bonding, ultrasonic bonding, welding, chemical bonding, felting, carding, airlaid, wetlaid, impaction, latex-bonding (e.g., by spraying web on top and bottom with a latex like styrene butadiene or acrylic, for instance), or any combination thereof. In some embodiments, the fibrous media is produced by airlaid or wetlaid methods, and can provide a curled fiber airlaid mat or a curled fiber wetlaid mat, respectively.

Figure 1B:
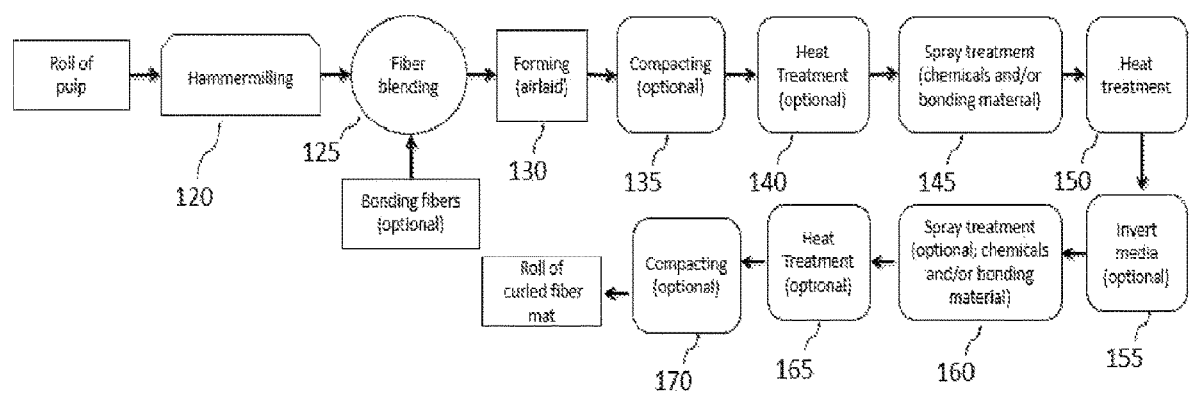

FIG. 1b depicts another embodiment for the present disclosure for producing a curled fiber mat. FIG. 1b, for instance, discloses an embodiment for manufacturing fibrous media via thermal bonding of untreated fibrous material (e.g., a roll of pulp).

The fibrous media used in any of the methods described herein can be produced by any method known in the art, including but not limited to needling, hydroentangling, adhesive bonding, spray bonding, thermal bonding, calendar bonding, through-air bonding, infrared bonding, ultrasonic bonding, welding, chemical bonding, felting, carding, airlaid, wetlaid, impaction, latex-bonding (e.g., by spraying web on top and bottom with a latex like styrene butadiene or acrylic, for instance), or any combination thereof. In some embodiments, the fibrous media is produced by airlaid or wetlaid methods, and can provide a curled fiber airlaid mat or a curled fiber wetlaid mat, respectively.

In some embodiments, the provided fibrous material at 102 can be in the form of a pulp. The pulp can be a fibrous pulp. The pulp can be from rice, wood, straw, switch grass, or other fibrous sources. The pulp can be a wood pulp, such as a chemical pulp from wood (e.g., softwood such as Southern bleached softwood kraft pulp) or mechanical pulp (e.g., softwood thermal mechanical pulp).

In some embodiments, the fibrous material comprises natural fibers, alone or in combination with natural non-wood alternative fibers, natural fibers, and/or manmade fibers. In some embodiments, the fibrous material includes cellulosic fibers. In some embodiments, the fibrous material comprises wood fibers. In some embodiments, the wood fibers can be provided in the form of a wood pulp or other fibrous source. For instance, the wood fibers can be provided in the form of southern bleached softwood kraft pulp. For instance, the wood fibers can be provided in the form of northern bleached softwood kraft pulp. For instance, the wood fibers can be provided in the form of mechanical pulp, e.g., thermo-mechanical pulp. Suitable examples of fibrous sources can include, but are not limited to, kraft pulp, fluff pulp, dissolving pulp, mechanical pulp, chemical pulp, chemical-mechanical pulp, recovered paper pulp, semi-mechanical pulp, semi-chemical pulp, soft cook fully chemical pulp, or any combination thereof. In some embodiments, the fibrous sources can comprise hardwood kraft pulp, softwood kraft (SWK) pulp, southern bleached SWK (SBSK or SBSWK) pulp, northern bleached SWK (NBSK or NBSWK), unbleached softwood kraft (UBSK or UBSWK), BCTMP (bleached chemi-thermomechanical pulp), TMP (thermomechanical pulp), and combinations thereof. Other non-limiting suitable examples of wood fibers include hardwood, softwood, aspen, balsa, beech, birch, mahogany, hickory, maple, oak, teak, *eucalyptus*, pine, fir, cedar, juniper, spruce, redwood, or any combination thereof. It is understood that any other known sources of wood fibers may be used. In some embodiments, the fibrous media can comprise fibrous material in the form of natural non-wood or alternative fibers. Suitable examples of natural non-wood alternative fibers that can make up the fibrous material in the fibrous media can include barley, bagasse, bamboo, wheat, flax, hemp, kenaf, *Arundo donax*, corn stalk, jute, ramie, cotton, wool, rye, rice, *papyrus*, esparto, sisal, grass, abaca, or a combination thereof. It is understood that the fibrous material can include any other natural fibers from any source or any combination of natural fibers. Other suitable non-limiting examples of fiber sources include consumer waste products such as clothes, tire silk, viscose, rayon, lyocell, or any combination thereof. In some embodiments, the fibrous material can be provided from cellulosic fibers that can be prepared from the wood pulp or otherwise provided fiber source by means of a mechanical process such as hammer-milling or other defibration processes.

In some embodiments, the fibrous material can further comprise man-made fibers. In some embodiments, the man-made fibers can include ceramic fibers, aramid fibers, polymer fibers, or any combination thereof. In some embodiments, the fibrous material comprises a man-made fiber to natural fiber ratio of 1:1 to 1:100 (e.g., 1:1.25, 1:5, 1:1.75, 1:2, 1:3, 1:4, 1:5, 1:6, 1:7, 1:8, 1:9, 1:10, 1:20, 1:30, 1:40, 1:50, 1:75, 1:100). The fibrous material can comprise any of the natural fibers disclosed herein in combination with any of the man-made fibers disclosed herein.

The fibrous material can include, by way of non-limiting example, pulp fibers, staple fibers, spun fibers, continuous filament fibers, or a combination thereof. For instance, the fibrous material can comprise natural staple fibers, continuous filament man-made fibers, or a combination thereof. In some embodiments, the fibrous material can comprise fibers having an average length from approximately 0.01 mm to 12 mm. For example, the fibrous material can comprise fibers having an average length of 0.01 mm or greater (e.g., 0.05 mm or greater, 0.10 mm or greater, 0.15 mm or greater, 0.20 mm or greater, 0.25 mm or greater, 0.30 mm or greater, 0.35 mm or greater, 0.40 mm or greater, 0.45 mm or greater, 0.50 mm or greater, 0.55 mm or greater, 0.60 mm or greater, 0.65 mm or greater, 0.70 mm or greater, 0.75 mm or greater, 0.80 mm or greater, 0.85 mm or greater, 0.90 mm or greater, 0.95 mm or greater, 1.0 mm or greater, 1.1 mm or greater, 1.2 mm or greater, 1.3 mm or greater, 1.4 mm or greater, 1.5 mm or greater, 1.6 mm or greater, 1.7 mm or greater, 1.8 mm or greater, 1.9 mm or greater, 2.0 mm or greater, 2.1 mm or greater, 2.2 mm or greater, 2.3 mm or greater, 2.4 mm or greater, 2.5 mm or greater, 2.6 mm or greater, 2.7 mm or greater, 2.8 mm or greater, 2.9 mm or greater, 3.0 mm or greater, 3.5 mm or greater, 4.0 mm or greater, 4.5 mm or greater, 5.0 mm or greater, 5.5 mm or greater, 6.0 mm or greater, 6.5 mm or greater, 7.0 mm or greater, 7.5 mm or greater, 8.0 mm or greater, 8.5 mm or greater, 9.0 mm or greater, 9.5 mm or greater, 10 mm or greater, 10.5 mm or greater, 11 mm or greater, or 11.5 mm or greater). In some embodiments, the fibrous material can comprise fibers having an average length of 12 mm or less (e.g., 11.5 mm or less, 11 mm or less, 10.5 mm or less, 10 mm or less, 9.5 mm or less, 9.0 mm or less, 8.5 mm or less, 8.0 mm or less, 7.5 mm or less, 7.0 mm or less, 6.5 mm or less, 6.0 mm or less, 5.5 mm or less, 5.0 mm or less, 4.5 mm or less, 4.0 mm or less, 3.5 mm or less, 3.0 mm or less, 2.9 mm or less, 2.8 mm or less, 2.7 mm or less, 2.6 mm or less, 2.5 mm or less, 2.4 mm or less, 2.3 mm or less, 2.2 mm or less, 2.1 mm or less, 2.0 mm or less, 1.9 mm or less, 1.8 mm or less, 1.7 mm or less, 1.6 mm or less, 1.5 mm or less 1.4 mm or less, 1.3 mm or less, 1.2 mm or less, 1.1 mm or less, 1.0 mm or less, 0.95 mm or less, 0.90 mm or less, 0.85 mm or less, 0.80 mm or less, 0.75 mm or less, 0.70 mm or less, 0.65 mm or less, 0.60 mm or less, 0.55 mm or less, 0.50 mm or less, 0.45 mm or less, 0.40 mm or less, 0.35 mm or less, 0.30 mm or less, 0.25 mm or less, 0.20 mm or less, 0.15 mm or less, 0.10 mm or less, 0.05 mm or less). In some embodiments, the fibrous material has a length of 0.01 mm to 12 mm (e.g., 0.3 mm to 7 mm, 0.5 mm to 5 mm, 0.7 mm to 2.8 mm, 2.9 mm to 8 mm, 8 mm to 12 mm, 0.01 mm to 1 mm). In some embodiments, the fibrous material has a length of 0.5 mm to 3 mm. In some embodiments, the fibrous material has a length of from about 2.0 mm to about 2.8 mm (e.g., for softwood pulp). In some embodiments, the fibrous material has a length of from about 0.8 mm to about 1.2 mm (e.g., for hardwood pulp). In some embodiments, the fibrous material comprises a blend of at least one fiber (natural and/or man-made) that are of different average fiber lengths. In other words, in some embodiments, the fibrous material has bimodal (or trimodal, etc.) fiber length distribution.

In some embodiments, the fibrous material can comprise fibers having various cross-sectional shapes (e.g., round, scalloped oval, cruciform, haxachannel, etc.). In some embodiments, the average linear density of the fibers in the fibrous material (i.e., the average linear density for a round fiber) is from 1.3 dtex to 2.7 dtex. In some embodiments, the fibrous material can have an average linear density of 1.3 (e.g., 1.4, 1.5, 1.6, 1.7, 1.8, 1.9, 2.0, 2.1, 2.2, 2.3, 2.4, 2.5, 2.6) dtex or greater. In some embodiments, the fibrous material can have an average linear density of 2.7 (e.g., 2.6, 2.5, 2.4, 2.3, 2.2, 2.1, 2.0, 1.9, 1.8, 1.7, 1.6, 1.5, 1.4) dtex or less. In some embodiments, the fibrous material can have an average linear density of 1.3 dtex to 2.7 dtex (e.g., 1.3 dtex to 2.0 dtex, 2.0 dtex to 2.7 dtex, 1.5 dtex to 2.5 dtex). In some embodiments, the fibrous material comprises a blend of at least one fiber (natural and/or man-made) that are of different average maximum cross-sectional size. In other words, in some embodiments, the fibrous material has bimodal (or trimodal, etc.) maximum cross-sectional size distribution.

In some embodiments, the fibrous material can comprise an additive. Additives can include, but are not limited to, bonding materials (e.g., bicomponent fibers), fillers (e.g., clay, carbonates), pigments, dyes, colorants, water repellants, grease repellants, antifungal agents, antibacterial agents, odor control agents, bioactive materials for sizing, biomaterials (e.g., lignin or other biopolymers) for bonding material as matrix, or a combination thereof. In addition, in some embodiments, the fibrous material is surface treated for functionality (e.g., water repellant) or decorative finish (e.g., bleaching, printing, etc.). In some embodiments, the additives include kaolin clay, china clay, calcium carbonate, titanium dioxide, and/or talc. Additives can be added to the fibrous material, for instance, using any method of combining fibrous material (defibered or otherwise) with another substance including, but not limited to, manual blending, mechanical blending, stirring, or combinations thereof.

In some embodiments, the bonding material comprises a bonding fiber. In some embodiments, the bonding fiber comprises a polymer. In some embodiments, the bonding fiber comprises a thermoplastic fiber. In some embodiments, the bonding fiber comprises a biodegradable fiber. The bonding fiber can include, but is not limited to, polyethylene, polyethylene terephthalate, polyester, polypropylene, polyvinyl chloride, polystyrene, polymethacrylate, polyethylene naphthalate, polyvinyl alcohol, polyurethane, polyacrylonitrile, polylactic acid (PLA), polyhydroxyalkanoates (PHA) or any combination thereof.

In some embodiments, the bonding fiber can comprise a monocomponent fiber. In some embodiments, the bonding fiber can comprise a bicomponent fiber. In some embodiments, the bonding fiber can comprise a tricomponent fiber. In some embodiments, the bonding fiber can comprise a mix of monocomponent fibers. In some embodiments, the bonding fiber can comprise a mix of bicomponent fibers. In some embodiments, the bonding fiber can comprise a mix of monocomponent fibers and bicomponent fibers. In some embodiments, the bonding fiber can comprise monocomponent fibers, bicomponent fibers, tricomponent fibers, or a combination thereof. Example bicomponent fiber configurations include, but are not limited to, core-sheath, side-by-side, segmented-pie, islands-in-the-sea, tipped, segmented-ribbon, or a combination thereof. A bicomponent fiber can include a fiber formed from two varieties of a single polymer type and can structurally comprise a core polymer and a sheath polymer. If the core and sheath polymers are varieties of the same polymer, they can retain their polymeric identity but have different melting points, which can render the bicomponent fibers useful as bonding agents. The core and sheath polymers can also comprise separate polymers. A person of ordinary skill in the art would recognize that the melting point of the sheath polymer varies depending on the composition of the sheath polymer, and that the bicomponent fibers can be heated in some embodiments to a temperature sufficient for bonding (e.g., above the melting point of the sheath polymer but below the melting temperature of the core polymer). As discussed in more detail below, the fibrous material and bonding fiber can form at least one layer of fibrous media and can be consolidated and/or processed (e.g., dried and/or cured) at a certain temperature. In some embodiments, the temperature used to consolidate and/or process the fibrous media can depend on the melting temperature of the bonding fiber of the fibrous media.

In some embodiments, the core of the bicomponent fiber can comprise at least one of polyester (which can have a melting temperature of from about 250° C. to about 280° C.), the sheath of the bicomponent fiber can be a polyethylene (which can have a melting temperature of from about 100° C. to about 115° C. for low-density polyethylene and from about 115° C. to about 180° C. for medium- to high-density polyethylene) and/or polypropylene (which can have a melting temperature of from about 130° C. to about 170° C.). In some embodiments, the bicomponent fibers can comprise a core polymer and a sheath polymer. In some embodiments, the core polymer can comprise at least one of a polyester, a polyethylene, and/or a polypropylene. In some embodiments, the core polymer can be selected from the group consisting of a polyester, a polyolefin, a polyethylene, a polypropylene, a polyethylene terephthalate, and a polybutylene terephthalate. In some embodiments, the sheath polymer can comprise at least one of a polyester, a polyethylene, and/or a polypropylene. In some embodiments, the sheath polymer can be selected from the group consisting of a polyester, a polyethylene, and a polypropylene. In some embodiments, the bicomponent fiber can comprise a polyester core and a polycaprolactone or polylactic acid sheath. In some embodiments, the bicomponent fiber can comprise a polyester core and a polyethylene sheath. In some embodiments, the bicomponent fiber can comprise a polypropylene core and a polyethylene sheath. In some embodiments, the bicomponent fiber can comprise a polyethylene terephthalate core and a polyethylene sheath. In some embodiments, the bicomponent fiber can comprise one or more biodegradable polymers. In some embodiments, the bicomponent fiber can comprise a polylactic acid core and a polybutylene succinate sheath. In some embodiments, the bicomponent fiber can be composed of a core polymer having a higher melting temperature than the sheath polymer. A person of ordinary skill in the art would recognize that any suitable bicomponent fiber, monocomponent fiber, or combination thereof would work in the embodiments disclosed herein and can include any thermoplastic polymer (or combination of thermoplastic polymers). In some embodiments, the bonding fiber is a tricomponent fiber (e.g., core-sheath-sheath). It is to be understood that any variety of polymers can be used in the bonding fiber, with any variety of properties and melting points, and in any configuration (e.g., monocomponent, bicomponent, islands-in-the-sea, etc.) to achieve the desired properties in the resulting product.

The bonding fiber can be provided in the form including, but not limited to, staple fibers, spun fibers, continuous filament fibers, or a combination thereof. In some embodiments, the bonding fiber has average length from 0.01 mm to 12 mm, including 0.5 mm to 12 mm. For example, the bonding fiber can have an average length of 0.01 mm or greater (e.g., 0.05 mm or greater, 0.10 mm or greater, 0.15 mm or greater, 0.20 mm or greater, 0.25 mm or greater, 0.30 mm or greater, 0.35 mm or greater, 0.40 mm or greater, 0.45 mm or greater, 0.50 mm or greater, 0.55 mm or greater, 0.60 mm or greater, 0.65 mm or greater, 0.70 mm or greater, 0.75 mm or greater, 0.80 mm or greater, 0.85 mm or greater, 0.90 mm or greater, 0.95 mm or greater, 1.0 mm or greater, 1.1 mm or greater, 1.2 mm or greater, 1.3 mm or greater, 1.4 mm or greater, 1.5 mm or greater, 1.6 mm or greater, 1.7 mm or greater, 1.8 mm or greater, 1.9 mm or greater, 2.0 mm or greater, 2.1 mm or greater, 2.2 mm or greater, 2.3 mm or greater, 2.4 mm or greater, 2.5 mm or greater, 2.6 mm or greater, 2.7 mm or greater, 2.8 mm or greater, 2.9 mm or greater, 3.0 mm or greater, 3.5 mm or greater, 4.0 mm or greater, 4.5 mm or greater, 5.0 mm or greater, 5.5 mm or greater, 6.0 mm or greater, 6.5 mm or greater, 7.0 mm or greater, 7.5 mm or greater, 8.0 mm or greater, 8.5 mm or greater, 9.0 mm or greater, 9.5 mm or greater, 10 mm or greater, 10.5 mm or greater, 11 mm or greater, or 11.5 mm or greater). In some embodiments, the bonding fiber can have an average length of 12 mm or less (e.g., 11.5 mm or less, 11 mm or less, 10.5 mm or less, 10 mm or less, 9.5 mm or less, 9.0 mm or less, 8.5 mm or less, 8.0 mm or less, 7.5 mm or less, 7.0 mm or less, 6.5 mm or less, 6.0 mm or less, 5.5 mm or less, 5.0 mm or less, 4.5 mm or less, 4.0 mm or less, 3.5 mm or less, 3.0 mm or less, 2.9 mm or less, 2.8 mm or less, 2.7 mm or less, 2.6 mm or less, 2.5 mm or less, 2.4 mm or less, 2.3 mm or less, 2.2 mm or less, 2.1 mm or less, 2.0 mm or less, 1.9 mm or less, 1.8 mm or less, 1.7 mm or less, 1.6 mm or less, 1.5 mm or less 1.4 mm or less, 1.3 mm or less, 1.2 mm or less, 1.1 mm or less, 1.0 mm or less, 0.95 mm or less, 0.90 mm or less, 0.85 mm or less, 0.80 mm or less, 0.75 mm or less, 0.70 mm or less, 0.65 mm or less, 0.60 mm or less, 0.55 mm or less, 0.50 mm or less, 0.45 mm or less, 0.40 mm or less, 0.35 mm or less, 0.30 mm or less, 0.25 mm or less, 0.20 mm or less, 0.15 mm or less, 0.10 mm or less, 0.05 mm or less). In some embodiments, the bonding fiber has a length of 0.01 mm to 12 mm (e.g., 0.3 mm to 7 mm, 0.5 mm to 5 mm, 0.7 mm to 2.8 mm, 2.9 mm to 8 mm, 8 mm to 12 mm, 0.01 mm to 1 mm). In some embodiments, the bonding fiber comprises a blend of at least one fiber (e.g., monocomponent fibers and bicomponent fibers, two different bicomponent fibers, two different monocomponent fibers) that are of different average fiber lengths. In other words, in some embodiments, the bonding fiber has bimodal (or trimodal, etc.) fiber length distribution. In some embodiments, the bonding fiber has a length of from about 3 mm to about 12 mm, including about 3 mm and about 6 mm.

In some embodiments, the bonding fiber can comprise fibers having various cross-sectional shapes (e.g., round, scalloped oval, cruciform, haxachannel, etc.). In some embodiments, the average maximum cross-sectional size of the fibers in the bonding fiber (i.e., the average diameter for a round fiber) varies depending on how the bonding fibers are made and can be manipulated to achieve different outcomes for the fibrous media or any intermediaries (e.g., layer of fibrous media) thereof. For instance, in some embodiments, the bonding fiber can comprise fibers of 1 dtex to 10 dtex (e.g., 1.3 dtex to 2.5 dtex, 5 dtex to 7 dtex). In some embodiments, the bonding fiber can comprise fibers of 1 dtex to 5 dtex, including 1.2 dtex, 2 dtex, and 4 dtex. In some embodiments, the bonding fiber can be crimped. In some embodiments, the bonding fiber can be uncrimped.

Any bonding material can be used that would provide the desired properties to the final product (e.g., curled fiber mat such as a curled fiber airlaid mat or curled fiber wetlaid mat) or any intermediary (e.g., fibrous media and/or treated fibrous media). In some embodiments, the bonding material comprises a bonding fiber as discussed herein. In some embodiments, the bonding material comprises a liquid binder. In some embodiments, the bonding material comprises a bonding fiber and liquid binder. In some embodiments, the bonding material comprises a resin (e.g., phenolic resin). In some embodiments, the resin is applied and dried without water. In some embodiments, the bonding material comprises a latex (e.g., styrene butadiene, acrylic). In some embodiments, the bonding material comprises a thermoplastic binder, wherein the mechanical properties of the thermoplastic binder can change with the temperature. In some embodiments, the bonding material comprises a thermoset binder, wherein the thermoset binder can be applied, dried, and/or heat-treated to become very hard and will no longer substantially change with temperature. Suitable examples of a liquid binder can include, but are not limited to, latex, styrene butadiene latex, styrene acrylic, polylactic acid, styrene maleic anhydride copolymer, styrene-acrylate copolymer, polyvinyl alcohol, carboxymethyl cellulose, hydroxymethyl cellulose, starch, dextrin, collagen, melamine, or a combination thereof.

In some embodiments, the liquid binder can be sprayed onto one or both sides of the fibrous material or fibrous media. The fibrous material or fibrous media can then be heated to dry the fibrous material or fibrous media and to enable the liquid binder to bind to the fibers of the fibrous material as well as to bind the fibers of the fibrous material together. The temperature and length of heating can depend on the type of liquid binder used, its concentration, and the amount of liquid binder applied to the fibrous material or fibrous media. If the fibrous material or fibrous media further comprises a bonding fiber, the temperature and length of heating can depend on the type of bonding fiber used. For example, if the bonding fiber comprises a bicomponent fiber, the temperature and length of heating can be optimized based on the core and sheath polymers of the bicomponent fiber. Further, the temperature and length of heating can depend on the amount of water or other liquid present in the fibrous material or fibrous media that needs to be evaporated prior to further processing steps. A person of ordinary skill in the art would understand how to optimize the heating step in order to dry and/or bond the fibrous material or fibrous media.

In some embodiments, the bonding material comprises a latex comprising polymer particles in an aqueous medium. In some embodiments, the polymer particles have an average particle size of 0.1 micron to 1 micron (e.g., 0.1 micron to 0.2 microns, 0.2 microns to 0.4 microns, 0.4 microns to 0.6 microns, 0.6 microns to 0.8 microns, 0.8 microns to 1 microns). In some embodiments, the polymer particles have an average particle size of 1 micron or less (e.g., 0.95 microns or less, 0.90 microns or less, 0.85 microns or less, 0.80 microns or less, 0.7 microns or less, 0.6 microns or less, 0.5 microns or less, 0.4 microns or less, 0.3 microns or less, 0.2 microns or less, 0.1 microns or less). In some embodiments, the polymer particles have an average particle size of 0.1 micron or greater (e.g., 0.95 microns or greater, 0.90 microns or greater, 0.85 microns or greater, 0.80 microns or greater, 0.7 microns or greater, 0.6 microns or greater, 0.5 microns or greater, 0.4 microns or greater, 0.3 microns or greater, 0.2 microns or greater). In some embodiments, the latex comprises a blend of one or more particles that are of different average particle size. In other words, in some embodiments, the latex has bimodal (or trimodal, etc.) particle size distribution.

In some embodiments, the bonding material comprises only a liquid binder. For example and not limitation, the binder comprises a latex (e.g., styrene butadiene, acrylic). In some embodiments, the binder comprises a thermoplastic binder, wherein the mechanical properties of the thermoplastic binder can change with the temperature. In some embodiments, the binder comprises a thermoset binder, wherein the thermoset binder can be applied, dried, and/or heat-treated to become very hard and will no longer substantially change with temperature. Suitable examples of a liquid binder can include, but are not limited to, latex, bio-based latex, styrene butadiene latex, acrylic latex, styrene acrylic, acrylic, polylactic acid, styrene maleic anhydride copolymer, styrene-acrylate copolymer, polyvinyl alcohol, carboxymethyl cellulose, hydroxymethyl cellulose, starch, dextrin, collagen, melamine, or a combination thereof. In some embodiments, the liquid binder can be sprayed onto one or both sides of the fibrous material or fibrous media. The fibrous material or fibrous media can then be heated to dry the fibrous material or fibrous media and to enable the liquid binder to bind to the fibers of the fibrous material as well as to bind the fibers of the fibrous material together. The temperature and length of heating can depend on the type of liquid binder used, its concentration, and the amount of liquid binder applied to the fibrous material or fibrous media. If the fibrous material or fibrous media further comprises a bonding fiber, the temperature and length of heating can depend on the type of bonding fiber used. For example, if the bonding fiber comprises a bicomponent fiber, the temperature and length of heating can be optimized based on the core and sheath polymers of the bicomponent fiber. Further, the temperature and length of heating can depend on the amount of water or other liquid present in the fibrous material or fibrous media that needs to be evaporated prior to further processing steps. A person of ordinary skill in the art would understand how to optimize the heating step in order to dry and/or bond the fibrous material or fibrous media.

The fibrous material or fibrous media can comprise the bonding fiber in any suitable amount to confer a desirable property to the fibrous media and/or any intermediaries (e.g., layer of fibrous media). In some embodiments, the fibrous media comprises no bonding fiber. In some embodiments, the bonding fiber is present in the fibrous media in an amount of 1% to 50% by weight, based on the total weight of the fibrous media. In some embodiments, the bonding fiber is present in the fibrous media in an amount of 5% to 30% by weight, based on the total weight of the fibrous media. In some embodiments, the bonding fiber is present in the fibrous media in an amount of 5% to 15% by weight based on the total weight of the fibrous media. In some embodiments which have bonding fiber in combination with a liquid binder, the bonding fiber can be present in a lower amount, such as less than 10% by weight based on the total weight of the fibrous media, preferably between 3% to 7% by weight.

Forming 104 shown in FIG. 1a or 130 in FIG. 1b can be, for instance, an airlaid process to produce a layer of airlaid media, or it can be a wetlaid process to produce a wetlaid media. In embodiments where the layer is an airlaid media, for instance, it can be formed in forming 104 or 130 using any device known in the art that can form an airlaid mat. In embodiments where the layer is a wetlaid media, for instance, it can be formed in forming 104 or 130 using any device known in the art that can form a wetlaid mat. Those skilled in the art would understand that an airlaid media or a wetlaid media can be formed by a device generally including a fiber feed for providing the fibrous material, a hammermill (e.g., a defibering process 120), a forming head for receiving the defibrated fibrous material and bonding fibers to form a web, and a conveyor on which the web is formed and compacted. In some embodiments, the fibrous material is provided in a defibered state and does not undergo the defibering process. In some embodiments, the fibrous material is provided in a fluffy or noncompacted state (e.g., not as a roll of fibrous material) and does not undergo the defibering process.

A person of ordinary skill in the art would understand that some or all process steps can have some or all features discussed above regarding the component parts. In some embodiments, the method can comprise forming the fibrous material, optionally compressing or compacting the fibrous material, bonding the fibrous material to form a fibrous media (e.g., an airlaid media or a wetlaid media), treating the fibrous media with chemicals such as additives and/or crosslinkers, heating and/or drying the fibrous media, and optionally compressing and heating the fibrous media. In some embodiments, for example when the fibrous material is cellulosic fiber and the bonding material is a bicomponent fiber, the fibrous material and bonding material can be bonded, treated, and heated and/or dried simultaneously. In some embodiments, the step of forming can further comprise compacting the fibrous material in the forming head. In some embodiments, for example when the fibrous material is cellulosic fiber and the bonding material is a liquid binder such as latex, the fibrous material and the bonding material can be bonded first and the treatment and heating and/or drying steps can be simultaneous. In some embodiments, the fibrous media can undergo multiple successive rounds of treatment and heating and/or drying. In some embodiments, the finished curled fiber mat can undergo a final compression with heating.

In FIG. 1b, a roll of pulp, which is an exemplary fibrous material, can be defibered (e.g., via hammermilling 120). Alternatively, the fibrous material can be defibered, or a fluffy/noncompacted pulp can be used. The defibered fluff pulp exiting hammermilling 120 can undergo fiber blending 125 with a bonding material. The blended fibers exiting fiber blending 125 can undergo forming 130 of a layer (e.g., an airlaid media or a wetlaid media). For example, the forming 130 can be done by one or more forming heads. If more than one forming head is used, each forming head can have the same fiber blend or a different fiber blend (e.g., a natural fiber blend or a man-made fiber blend, or a first head can have one type of natural fiber and a second head can have a different type of natural fiber). The conditions of the forming step (e.g., rate of mat formation) can be optimized based on the general knowledge of one of ordinary skill in the art. The formed layer exiting the forming step 130 can then undergo optional compaction 135 by a roller that can be heated, and nipped with a backing roller, optional heat treatment 140, spray treatment 145 (e.g., spray treatment for flame resistance), and/or a heat treatment 150 to produce a roll of fibrous media. The compacting roller can optionally be engraved. Additional bonding fibers can be added in the fiber blending step 125 before the forming process which can produce a fiber media comprising a bonding material and a binder (e.g., the bonding material can comprise bicomponent fibers and the binder can comprise a polymer such as latex). The conditions used in the spray treatment as well as the specific treatment used can depend on the selected chemical and its concentration. The temperature used in the heat treatment(s) can depend on the chemical added during the spray treatment as well as the concentration of the chemical. The time of the heat treatment(s) can also depend on the chemical added during the spray treatment and its concentration. Further, the temperature and time of the heat treatment can be optimized based on the bonding material in order to bond the layer. For example, the time and temperature can be selected based on the specific type of bonding material, e.g., the sheath and core polymers of a bicomponent fiber can be used to determine the heating conditions, or the type and concentration of liquid binder can be used to determine the heating conditions. The temperature and time of the heat treatment(s) can also be optimized based on the amount of water or aqueous solution that needs to be evaporated from the fibrous media. The pressure applied by the compacting roller in optional compaction step 135 or in the optional final compaction step 170 can be optimized based on, for example and not limitation, the desired decrease in caliper of the mat. Any of the heat treatment step(s) can be a drying step and/or a curing step.

In some embodiments, the fibrous material (e.g., a roll of pulp) can undergo a defibration process. For example, the fibrous material can be hammermilled 120. As would be appreciated by one of ordinary skill in the art, the defibration process can better prepare the fibrous material to be formed into a layer and allow for better control over fibrous material parameters such as fiber length, and knot content. Nonlimiting examples of a defibration process can include hammermilling, grinding, and/or crushing. In some embodiments, the fibrous material is already defibered and does not need to undergo the defibration process. In still other embodiments, the fibrous material is provided in a fluffy or noncompacted form, e.g., is provided directly from a drying process and is not compacted into a roll or bale, and does not undergo the defibration process.

Fiber blending step 125 can include, for instance, any method of combining fibrous material, including natural and/or man-made fibers, in any combination (defibered or otherwise), with another substance including, but not limited to, bonding material. Nonlimiting fiber blending processes include, but are not limited to, manual blending, mechanical blending, stirring, or combinations thereof.

Forming step 130 can be, for instance, an airlaid process to produce a layer of airlaid media. In embodiments where the layer is an airlaid media, for instance, it can be formed using any device known in the art that can form an airlaid media, such as for example and not limitation a drumformer or a spike former, under conditions that can be optimized by one of skill in the art. Forming step 130 can also be, for instance, a wetlaid process to produce a layer of wetlaid media. In embodiments where the layer is a wetlaid media, for instance, it can be formed using any device known in the art that can form a wetlaid media. Those skilled in the art would understand that an fibrous media layer can be formed by a device generally including a fiber feed for providing the fibrous material, a hammermill (e.g., a defibering process), at least one forming head for receiving the defibrated fibrous material and bonding fibers to form a web of the fibrous material, and a conveyor on which the web of fibrous material is formed and compacted into a mat. In some embodiments, the fibrous media layer can be formed from a fibrous material that has already been defibered and thus does not need to undergo a defibering process. In some embodiments, the fibrous media layer can be formed from a fluffy or uncompacted fibrous material, e.g., one that has not been compacted into a bale or roll. In some embodiments, the mat can be initially compacted by applying a vacuum in the forming head pulling from under the forming wire. The degree of initial compaction can be affected by adjusting the level of the vacuum in the forming head. Additional optional compaction 135 of the media can be performed after forming by a roller, which can optionally be engraved and/or heated. The pressure applied by the roller can be optimized based on, for example and not limitation, the desired decrease in caliper of the fibrous media. The pressure can be applied in addition to the weight of the roller itself. In some embodiments, the caliper of the media can be decreased by about 10% to about 50%. In some embodiments, the compaction step can be performed later in the process, e.g., to the final curled fiber mat. The mat can undergo nipping with a backing roller after the optional compaction.

In some embodiments, the forming 130 can be done by one or more forming heads. If more than one forming head is used, each forming head can have the same fiber blend or a different fiber blend (e.g., a natural fiber blend or a man-made fiber blend, or a first head can have one type of natural fiber and a second head can have a different type of natural fiber).

The fibrous media can be made of various thicknesses. In some embodiments, the fibrous media has a thickness of 0.5 mm (e.g., 1 mm, 2 mm, 3 mm, 4 mm, 5 mm, 6 mm, 7 mm, 8 mm, 9 mm, 10 mm, or 11 mm) or greater. In some embodiments, the fibrous media has a thickness of 12 mm (e.g., 1 mm, 2 mm, 3 mm, 4 mm, 5 mm, 6 mm, 7 mm, 8 mm, 9 mm, 10 mm, or 11 mm) or less. In some embodiments the fibrous media has a thickness of 0.5 mm to 12 mm (e.g., 0.5 mm to 1 mm, 1 mm to 2 mm, 2 mm to 3 mm, 0.5 mm to 3 mm, 3 mm to 8 mm, 8 mm to 10 mm, 10 mm to 12 mm, 9 mm to 11 mm, 8 mm to 12 mm).

In some embodiments, the fibrous media can have a weight of 40 gsm (grams per square meter) to 700 gsm, as measured by PAPTAC Standard D.3 (2011). For instance, in some embodiments for acquisition and distribution layers, the fibrous media can have a weight of 40 gsm to 110 gsm.

In some embodiments comprising an integral acquisition and distribution layer and absorbent core, the fibrous media can have a weight of 100 gsm to 700 gsm. For instance, the fibrous media can have a weight of 60 (e.g., 70, 80, 90, 100, 110, 120, 130, 140, 150, 160, 170, 180, 190, 200, 225, 250, 275, 300, 325, 350, 375, 400, 425, 450, 475, 500, 525, 550, 575, 600, 625, 650, 675) gsm or greater. For instance, the fibrous media can have a weight of 700 (e.g., 70, 80, 90, 100, 110, 120, 130, 140, 150, 160, 170, 180, 190, 200, 225, 250, 275, 300, 325, 350, 375, 400, 425, 450, 475, 500, 525, 550, 575, 600, 625, 650, 675) gsm or less. For instance, the fibrous media layer can have a weight of from 60 gsm to 700 gsm (e.g., 60 gsm to 110 gsm, 60 gsm to 90 gsm, 90 gsm to 110 gsm, 100 gsm to 700 gsm, 100 gsm to 400 gsm, 400 gsm to 700 gsm, 250 gsm to 650 gsm). A person of ordinary skill in the art would recognize that the weight of the fibrous media can be expanded above or below the ranges (above in this paragraph) as needed for various other applications and uses.

In some embodiments, the fibrous media can also comprise super absorbent polymer (SAP) particles. SAP particles are generally found in fibrous media for use in the absorbent core of certain absorbent articles. The SAP particles can be present in an amount of 0% to 70% by weight of the fibrous media in the absorbent core, such as 30% to 50% SAP particles by weight of the fibrous media in the core.

In some embodiments, the fibrous media can undergo at least one heat treatment. In some embodiments, the heat treatment is used to bond or consolidate the fibrous media. In some embodiments, the fibrous media can undergo heat treatment to a certain temperature. In some embodiments, the conditions of the heat treatment (e.g., temperature and time) can be selected and optimized based on the bonding material, e.g., a bicomponent fiber and/or a liquid binder. In some embodiments, the conditions of the heat treatment (e.g., temperature and time) can be selected and optimized based on the amount of water or other liquid to be evaporated prior to proceeding with processing. In some embodiments, the heating can be performed in a hot press, an infrared system, or an oven (e.g., a through-air drying oven). The conditions of the heat treatment can further depend on the source of the heat. For example, if a through-air drying oven is used, one of ordinary skill in the art will understand how to select the temperature, air velocity, time, and speed of the oven in order to achieve the desired results. In some embodiments, the temperature chosen can be based on the melting temperature of the bonding materials. In some embodiments, the temperature chosen is at or above the melting temperature of the bonding material (e.g., bonding fibers). In embodiments where the bonding materials are bicomponent fibers, the temperature can be chosen to be at or above the melting temperature of the sheath of the bicomponent fiber, for instance, as discussed above. In some embodiments, the temperature is chosen such that the sheath polymer of the bicomponent fiber is partially melted or fully melted. In some embodiments, the temperature can be from 40° C. to 200° C. (e.g., 40° C. to 50° C., 50° C. to 100° C., 100° C. to 140° C., 140° C. to 200° C., 150° C. to 175° C.). In some embodiments, the temperature is 40° C. or greater (e.g., 50° C. or greater, 60° C. or greater, 70° C. or greater, 80° C. or greater, 90° C. or greater, 100° C. or greater, 110° C. or greater, 120° C. or greater, 130° C. or greater, 140° C. or greater, 150° C. or greater, 160° C. or greater, 170° C. or greater, 180° C. or greater, 190° C. or greater). In some embodiments, the temperature is 200° C. or less (e.g., 50° C. or less, 60° C. or less, 70° C. or less, 80° C. or less, 90° C. or less, 100° C. or less, 110° C. or less, 120° C. or less, 130° C. or less, 140° C. or less, 150° C. or less, 160° C. or less, 170° C. or less, 180° C. or less, 190° C. or less). In some embodiments, the temperature is chosen based on at least the bonding material and/or heat source. In some embodiments, the temperature is chosen based on at least the amount of water or other liquid to be evaporated from the fibrous media.

In some embodiments, the fibrous media is heated for a period of time. In some embodiments, the period of time is an amount of time sufficient to fully melt (e.g., liquefy) or partially melt (e.g., soften, render tacky) the bonding fiber. In some embodiments, the layer(s) of fibrous media and/or other layers are heated for a period of time to consolidate the layer(s) of fibrous media and/or other layers to form a consolidated mat. In some embodiments, the period of time is 1 second to 10 minutes (e.g., 5 seconds to 10 seconds, 10 seconds to 20 seconds, 20 seconds to 30 seconds, 30 seconds to 45 seconds, 45 seconds to 60 seconds, 60 seconds to 90 seconds, 90 seconds to 120 seconds, 30 seconds to 120 seconds, 1 minute to 2 minutes, 1 minute to 5 minutes, 5 minutes to 10 minutes). In some embodiments, the period of time is 1 second or greater (e.g., 10 seconds or greater, 20 seconds or greater, 30 seconds or greater, 40 seconds or greater, 50 seconds or greater, 1 minute or greater, 2 minutes or greater, 4 minutes or greater, 6 minutes or greater, 8 minutes or greater). In some embodiments, the period of time is 10 minutes or less (e.g., 1 minute or less, 2 minutes or less, 4 minutes or less, 6 minutes or less, 8 minutes or less). In some embodiments, the heating time is chosen based on at least the bonding material and/or heat source. In some embodiments, the heating time is chosen based on at least the amount of water or other liquid to be evaporated from the fibrous media.

In some embodiments, the fibrous media can be manufactured from a fibrous material and a bonding material comprising a liquid binder. In some embodiments, the fibrous material can be formed into a layer using an aforementioned nonwoven process, such as airlaying or wetlaying. In some embodiments, the liquid binder can be applied to the layer using an aforementioned coating or liquid impregnation process. In some embodiments, a chemical (e.g., a crosslinker) can be applied to the layer. In some embodiments, the liquid binder and the chemical (e.g., a crosslinker) can be applied to the layer simultaneously.

In some embodiments, the fibrous media can be manufactured from a combination of a fibrous material with a bonding material comprising both bonding fibers and a liquid binder. In some embodiments, the bonding fibers comprise monocomponent fibers, bicomponent fibers, tricomponent fibers, and combinations thereof. In some embodiments, the fibrous material can be formed into a layer using an aforementioned nonwoven process, such as airlaying or wetlaying. In some embodiments, the liquid binder can be applied to the layer using an aforementioned coating or liquid impregnation process. In some embodiments, a chemical (e.g., a crosslinker) can be applied to the layer. In some embodiments, the liquid binder and the chemical (e.g., a crosslinker) can be applied to the layer simultaneously.

In some embodiments, the bonding material is combined with the fibrous material in the layer through a combining process. Nonlimiting examples of a combining process to combine the bonding fiber and the fibrous material include needling, hydroentangling, adhesive bonding, spray bonding, thermal bonding, calendar bonding, through-air bonding, infrared bonding, ultrasonic bonding, welding, chemical bonding, felting, carding, airlaid, wetlaid, impaction, latex-bonding (e.g., by spraying web on top and bottom with a latex like styrene butadiene or acrylic, for instance), or any combination thereof.

The fibrous media can also include additives. In some embodiments, the additives can be introduced with the fibrous material and/or the bonding material. In some embodiments, the additives can be introduced during the airlaying or wetlaying process. In some embodiments, the additives can be applied to the fibrous media after its formation. In some embodiments, the additives include fillers (e.g., clay, carbonates), pigments, dyes, colorants, water repellants, grease repellants, antifungal agents, antibacterial agents, odor control agents, bioactive materials for sizing, biomaterials (e.g., lignin or other biopolymers) for bonding material as matrix, or a combination thereof. In addition, in some embodiments, the fibrous media is surface treated for functionality (e.g., water absorbency) or decorative finish (e.g., bleaching, embossing, printing, etc.) as shown in FIG. 1b at 145. In some embodiments, the additives include kaolin clay, china clay, calcium carbonate, titanium dioxide, and/or talc.

After the fibrous media is formed, it can be treated with a chemical such as an additive or a crosslinking agent at 106 or 145 in FIGS. 1a and 1b, respectively. In some embodiments, the treatment includes spray treating the fibrous material with a bonding material, a crosslinking agent, an additive, or a combination thereof. In some embodiments, the fibrous materials are surface treated to improve the chemical and/or mechanical properties of the fibrous materials or fibrous media. The fibrous materials can be surface treated using chemical and/or physical surface treatments. In some embodiments, the surface treatment includes adhesive treatment, adding/removing static charges between fibers, electric discharge, mercerization, graft copolymerization, peroxide treatment, vinyl grafting, bleaching, acetylation, coupling-agent treatment, isocyanate treatment, addition of colorants, or combinations thereof. In some embodiments, the fibrous materials are surface treated to increase the bonding between the fibrous material and bonding fiber, decrease static between fibers, change the physical appearance of the fibers, and various other property enhancements known to those of ordinary skill in the art. The conditions of the surface treatment(s) are selected based on the specific composition being applied to the fibrous materials and/or its concentration. The conditions of the heat treatment(s) are also selected based on the specific composition being applied to the fibrous materials and/or its concentration. In some embodiments, the starting material (e.g., pulp, defibered pulp, fluffy pulp) has already been surface treated, particularly surface treatments for lowering static charge, altering hydrophobicity, and/or providing odor control, antibacterial properties, and/or antifungal properties.

In embodiments using a crosslinking agent, the crosslinking agent can create permanent curl in the fibers of the fibrous media, which can allow the disposable article and/or acquisition and distribution layer to effectively handle multiple liquid insults. The crosslinking agent can be applied to the fibrous media in any manner known to a person of ordinary skill in the art. In some embodiments, the crosslinking agent is applied via spray treatment. In some embodiments, the crosslinking agent is applied as a foam treatment. In some embodiments, the crosslinking agent is applied as a coating.

The crosslinking agent can be any crosslinking agent suitable for crosslinking fibers of a fibrous media, including urea-based crosslinkers, dialdehyde crosslinkers, glyoxal-urea adducts, polycarboxylic acids, and polymeric polycarboxylic acids. Non-limiting examples include the lists of crosslinking agents in U.S. Pat. No. 7,018,508 and references cited therein, which are incorporated herein by reference in their entireties. In some embodiments, the crosslinking agent can be glutaraldehyde and/or citric acid and/or sodium hypophosphite. The crosslinking agent can be added in an amount of 1% (e.g., 1%, 3%, 4%, 5%, 6%, 7%, 8%, 9%, 10%, 20%) or greater crosslinking agent, based on weight of the fibrous material in the fibrous media. The crosslinking agent can be added in an amount of 20% (e.g., 1%, 3%, 4%, 5%, 6%, 7%, 8%, 9%, 10%, 11%) or less crosslinking agent, based on weight of the fibrous material in the fibrous media. In an embodiment, the crosslinking agent can be added in an amount of 1% to 20% by weight, 1% to 10% by weight, 1% to 8% by weight, 1% to 6% by weight, 1% to 5%, 2% to 6% by weight, or 3% to 6% by weight, on the basis of the fibrous material in the fibrous media. In some embodiments, the crosslinking agent comprises 5% to 7.5% based on the weight of the fibrous material on one or both sides of the fibrous material, for a total of 5% to 15% by weight of the fibrous material. In some embodiments, the crosslinking agent comprises 3.5% to 5% (e.g., 3.6%, 3.7%, 3.8%, 3.85%, 3.9%, 4%, 4.1%, 4.2%, 4.3%, 4.4%, 4.5%, 4.6%, 4.7%, 4.8%, 4.9%) of citric acid, by weight of the fibrous material in the fibrous media. In some embodiments, the crosslinking agent comprises 1% to 2.5% (e.g., 1.1%, 1.15%, 1.2%, 1.3%, 1.4%, 1.5%, 1.6%, 1.7%, 1.8%, 1.9%, 2%, 2.1%, 2.2%, 2.3%, 2.4%) of glutaraldehyde, by weight of the fibrous material in the fibrous media.

In an embodiment, the crosslinking agent can be citric acid (including salts of citric acid). The citric acid can be added in an amount at least 0.5% by weight, or in an amount of 0.5%-20% by weight, or in the amounts further described above. In an embodiment the crosslinking agent can include citric acid and further include a hypophosphite, such as for example and not limitation, sodium hypophosphite. The ratio of citric acid to hypophosphite to base can be 1 citric acid to 0.2-0.4 hypophosphite, by weight of the fibrous material. In some embodiments, the citric acid and/or sodium hypophosphite can be added in amounts of 5% to 7.5% based on the weight of the fibrous material on one or both sides of the fibrous material, for a total of 5% to 15% by weight of the fibrous material.

In an embodiment, the crosslinking agent can include citric acid, a hypophosphite, and a base (e.g., citric acid, sodium hypophosphite and sodium hydroxide). The ratio of citric acid to hypophosphite to base can be 1 citric acid to 0.2-0.4 hypophosphite to 0.05 to 0.15 base (e.g., 1:0.2-0.4: 0.05-0.15, 1:0.3:0.1), by weight of the fibrous material. In some embodiments, there is no base. A base can be used in some embodiments, for instance, to adjust pH (e.g., for decreasing urine smell, promoting skin health, etc.).

In some embodiments, the total amount of crosslinking agent and hypophosphite is 3% to 20% (e.g., 3% to 5%, 5% to 15%, 8% to 11%, 12% to 15%, 7% to 12%), based on the weight of the fibrous material. In some embodiments, the total amount of crosslinking agent and hypophosphite is 3% (e.g., 4%, 5%, 6%, 7%, 8%, 9%, 10%, 11%, 12%, 13%, 14%) or greater, based on the weight of the fibrous material. In some embodiments, the total amount of crosslinking agent and hypophosphite is 20% (e.g., 4%, 5%, 6%, 7%, 8%, 9%, 10%, 11%, 12%, 13%, 14%) or less, based on the weight of the fibrous material. In some embodiments, the total amount of crosslinking agent and hypophosphite can comprise 7.5% w/w of citric acid and catalyst relative to the weight of the fibrous material (e.g., a 100 gsm fibrous medium can be treated with 7.5 grams of the chemicals on a dry basis on at least one side). In some embodiments, more than one side of the fibrous material can be treated with the crosslinking agent and hypophosphite, for a total of 5% to 20% by weight of the fibrous material. In some embodiments, the fibrous media can be treated with the crosslinking agent and hypophosphite on one side. In some embodiments, the fibrous media can be treated with the crosslinking agent and hypophosphite composition on more than one side. If the fibrous media is treated on more than one side, less of the crosslinking agent and hypophosphite composition can be used. For example, two sides of the fibrous media can each be treated with 2.5% w/w of the crosslinking agent and hypophosphite composition (total 5% w/w of the crosslinking agent and hypophosphite composition). In some embodiments, two sides of the fibrous media can each be treated with 7.5% w/w of the crosslinking agent and hypophosphite composition (total 15% w/w of the crosslinking agent and hypophosphite composition. In some embodiments, two sides of the fibrous media can each be treated with 2.5% w/w to 7.5 w/w of the crosslinking agent and hypophosphite composition (total 5% w/w to 15% w/w of the crosslinking agent and hypophosphite composition. In some embodiments, one side of the fibrous media can be treated with 2.5% w/w to 20% w/w of the crosslinking agent and hypophosphite composition.

The ratio of citric acid:hypophosphite:base can be based on weight of the fibrous material, assuming that the components are citric acid:sodium hypophosphite:sodium hydroxide. However, other compounds might be used that can still fulfill the chemical reactivity required. For example, instead of sodium hydroxide (MW=40), a person of ordinary skill could substitute potassium hydroxide (MW=56), and would recalculate the amount of base needed as 1.4 times higher, based on conversion 1 equivalent NaOH/40=x equivalents KOH/56. Similarly, other bases or other hypophosphites could be used. Moreover, citric acid and a base can react to form a citrate salt, such as with citric acid and sodium hydroxide to form sodium citrate having up to three sodiums per citrate depending on the number of acid groups neutralized. Thus, the ratio above also is intended to describe a ratio of components even when a citrate salt is used in place of, or a partial replacement of, citric acid and/or a base. One of ordinary skill would understand how to convert the molecular weights of components to apply to the weight ratio provided above. In some embodiments, no base is used.

After addition of the crosslinking agent, the treated fibrous media can be dried. In some embodiments, the conditions of the drying (e.g., temperature and time) can be selected an optimized based on the amount of water or other liquid to be evaporated prior to proceeding with processing. In some embodiments, the drying can be performed in a hot press, an infrared system, or an oven (e.g., a through air drying oven). The drying can occur at, for instance, a temperature of 100° C. (e.g., 110° C., 120° C., 130° C., 140° C., 150° C., 160° C.) or greater. The drying can occur at, for instance, a temperature of 160° C. (e.g., 110° C., 120° C., 130° C., 140° C., 150° C., 160° C.) or less. The drying can occur for a time of 10 seconds (e.g., 12 seconds, 15 seconds, 20 seconds, 25 seconds, 30 seconds, 35 seconds, 40 seconds, 45 seconds, 50 seconds, 55 seconds, 60 seconds, 65 seconds, 70 seconds, 75 seconds, 80 seconds, 85 seconds) or greater. The drying can occur for a time of 90 seconds (e.g., 12 seconds, 15 seconds, 20 seconds, 25 seconds, 30 seconds, 35 seconds, 40 seconds, 45 seconds, 50 seconds, 55 seconds, 60 seconds, 65 seconds, 70 seconds, 75 seconds, 80 seconds, 85 seconds) or less. A person of ordinary skill in the art will know how to optimize the conditions (e.g., the temperature, type of heating device, time, etc.) of the drying step in order to achieve the desired results. For example, if the fibrous media is being treated on more than one side, each side can be treated and/or dried separately. Alternatively, depending on the strength of the fibrous media (e.g., if it has been bonded or if it is sufficiently strong), it is possible to treat both sides of the fibrous media at the same time and then dry the fibrous media.

The treated fibrous media can also be cured. By "cured" is meant a final drying process that reduces the water level to less than 10% water, less than 8% water, less than 6% water, or less than 2% water. "Cured" can also indicate that the chemical crosslinking is substantially complete, such as at least 75% complete, 80% complete, 85% complete, 90% complete, or 95% complete. The curing can occur at, for instance, 145° C. (150° C., 155° C., 160° C., 165° C., 170° C., 175° C., 180° C., 185° C., 190° C., 195° C., 200° C.) or greater. The curing can occur at, for instance, 210° C. (150° C., 155° C., 160° C., 165° C., 170° C., 175° C., 180° C., 185° C., 190° C., 195° C., 200° C.) or less. The curing time can decrease as the curing temperature increases. For example, curing can occur at 180° C. for about 5 minutes, at 195° C. for 1.5 minutes, or at 200° C. for 1 minute. A person of ordinary skill in the art will know how to optimize the conditions (e.g., the temperature, type of heating device, time, etc.) of the curing step in order to achieve the desired results. For example, the curing can be for a time from 30 seconds to 6 minutes, such as from 1 minute to 5 minutes or from 1.5 minutes to 2 minutes.

Depending on the process scheme, the drying temperature and the curing temperature can be the same temperature or different temperatures. For example, the drying can occur in a dryer, e.g., a through-air drying oven, where the air in the dryer operates at between 170° C. and 200° C., and the curing can occur in an oven at 170° C. to 200° C. Alternatively, the air temperature in the through-air drying oven could be higher or lower than the air temperature during curing. Moreover, one of ordinary skill would recognize that the internal temperature of the treated fibrous media can be different than the air temperature. In some embodiments, the drying occurs before and separate from the curing. In some embodiments, the drying and curing occur simultaneously or in an overlapping manner. A person of ordinary skill in the art will know how to optimize the drying and curing steps, and how to determine if they should be separate, simultaneous, or overlapping. Such a person will understand how to select the temperature, type of heating device, time, and other conditions in order to achieve the desired results in either or both of the drying and/or curing steps.

In some embodiments, moisture is added back in after drying and/or curing, e.g. to 5% to 10% moisture (e.g., 5%, 6%, 7%, 8%, 9%, 10%), by weight of the fibrous material. In some embodiments, the moisture is added back in a cooling zone in the through-air drying oven.

In general, the term curl index or curl index value refers to the length weighted curl index. Curl index is measured for fibers according to standards used in the industry. The curl index is typically measured with a Fiber Quality Analyzer, such as an instrument by OpTest. Generally, the curl index (length weighted, unless otherwise specified) is determined by standard procedures. The curl index is determined by measuring individual fiber contours and projected lengths using optically imaged fibers, such as with a CCD camera and polarized infrared light. The curl index, CI, is determined by:

$$CI = \frac{L}{l} - 1$$

where L=contour length and l=projected length. The length weighted curl index (LWCI) is calculated by multiplying the sum of the individual CI by its contour length and dividing by the summation of the contour lengths:

$$LWCI = \frac{\sum_i CI_i * L_i}{\sum_i L_i}$$

where $CI_i$=individual arithmetic curl index and $L_i$=individual contour length.

The curled fiber mats disclosed herein can have a curl index of 0.28 (e.g., 0.29, 0.3, 0.31, 0.32, 0.33, 0.34, 0.35, 0.36) or greater. The curled fiber mats disclosed herein can have a curl index of 0.37 (e.g., 0.29, 0.3, 0.31, 0.32, 0.33, 0.34, 0.35, 0.36) or less.

The curled fiber mats disclosed herein can have a very long-lasting or even permanent curl resulting from the crosslinking treatment, as described in U.S. Pat. No. 10,266,989. A curl resulting from crosslinking treatments generally does not collapse when insulted with liquid, whereas a curl resulting from mechanical or thermal treatment may collapse upon such insult.

The curled fiber mats disclosed herein can be made by a variety of processes, including but not limited to airlaid or wetlaid processes.

The curled fiber mat can be made of various thicknesses. In some embodiments, the curled fiber mat has a thickness of 0.5 mm (e.g., 2 mm, 3 mm, 4 mm, 5 mm, 6 mm, 7 mm, 8 mm, 9 mm, 10 mm, or 11 mm) or greater. In some embodiments, the curled fiber mat has a thickness of 12 mm (e.g., 2 mm, 3 mm, 4 mm, 5 mm, 6 mm, 7 mm, 8 mm, 9 mm, 10 mm, or 11 mm) or less. In some embodiments the curled fiber mat has a thickness of 1 mm to 12 mm (e.g., 1 mm to 2 mm, 2 mm to 3 mm, 1 mm to 3 mm, 3 mm to 8 mm, 8 mm to 10 mm, 10 mm to 12 mm, 9 mm to 11 mm, 8 mm to 12 mm).

In some embodiments, the curled fiber mat can have a weight of 10 gsm (grams per square meter) to 200 gsm, as measured by PAPTAC Standard D.3 (2011). For instance, the curled fiber airlaid mat can have a weight of 10 gsm or greater (e.g., 20 gsm or greater, 30 gsm or greater, 40 gsm or greater, 50 gsm or greater, 60 gsm or greater, 70 gsm or greater, 80 gsm or greater, 90 gsm or greater, 100 gsm or greater, 110 gsm or greater, 120 gsm or greater, 130 gsm or greater, 140 gsm or greater, 150 gsm or greater, 160 gsm or greater, 170 gsm or greater, 180 gsm or greater, or 190 gsm or greater). For instance, the curled fiber mat can have a weight of 200 gsm or less (e.g., 20 gsm or less, 30 gsm or less, 40 gsm or less, 50 gsm or less, 60 gsm or less, 70 gsm or less, 80 gsm or less, 90 gsm or less, 100 gsm or less, 110 gsm or less, 120 gsm or less, 130 gsm or less, 140 gsm or less, 150 gsm or less, 160 gsm or less, 170 gsm or less, 180 gsm or less, or 190 gsm or less). For instance, the curled fiber mat layer can have a weight of from 10 gsm to 200 gsm (e.g., 10 gsm to 40 gsm, 40 gsm to 100 gsm, 60 gsm to 120 gsm, 65 gsm to 95 gsm, 75 gsm to 85 gsm, 80 gsm to 90 gsm, 90 gsm to 100 gsm, 10 gsm to 100 gsm, 100 gsm to 150 gsm, or 150 gsm to 200 gsm). A person of ordinary skill in the art would recognize that the weight of the curled fiber mat can be expanded above or below the ranges (above in this paragraph) as needed for various other applications and uses.

In some embodiments, the process 100 further comprises an additional surface treatment to the fibrous material including, but not limited to, spray treating the fibrous material with one or more of a bonding material, an odor control material, an antibacterial agent, an antifungal agent, a hydrophobicity-altering agent, or a combination thereof. In some embodiments, the fibrous materials are surface treated to improve the chemical and/or mechanical properties of the fibrous materials or resulting product. The fibrous materials can be surface treated using chemical and/or physical surface treatments. The treatment can be applied to one or more than one side of the fibrous material.

The method of this disclosure also produces a pulp with permanent curl. It may also produce pulp, in some embodiments, with low water retention values (WRV). Water retention value is typically measured in the industry using TAPPI Method UM256. In many products such as diapers, an absorbent pad typically consisting of pulp fiber and superabsorbent is used to absorb liquid insults. This absorbent pad can sometimes not absorb the insult rapidly enough at the point of insult due to gel blocking or other limitations of pad, which leads to leaks. To reduce leakage a layer is added on top of the absorbent pad commonly referred to as an acquisition and distribution layer (ADL). This ADL spreads the insult in the x-y plane of the layer increasing the area of the absorbent pad below that is exposed to the insult. This in turn reduces gel blocking and reduces the potential for leakage. In some embodiments, crosslinked mechanically treated pulp used in the ADL can have a water retention value of 0.30 (e.g., 0.28, 0.25) or less, as measured according to TAPPI Method UM256.

Also disclosed herein are products made by the methods disclosed herein. In some embodiments, the products include disposable absorbent articles (e.g., diapers, feminine hygiene products, hospital gowns, food-packing absorbent articles). In some embodiments, the products include acquisition and distribution layers. In some embodiments, the products include acquisition and distribution layers and an absorbent core. In some embodiments, the products include acquisition and distribution layers and a separate absorbent core.

In some embodiments disclosed herein, e.g. as shown in FIG. 1a, the fibrous media formed at 104 (130 of FIG. 1b) is of a thickness such that it is intended to function as an integral absorbent core and acquisition and distribution layer, wherein a portion (e.g., one surface) of the fibrous media is treated with the crosslinking agent. In some embodiments with an integral absorbent core and acquisition and distribution layer, the portion of the fibrous media that is treated with the crosslinking agent may have partial penetration of the crosslinking agent into the fibrous media (e.g., 5%, 8%, 10%, 12%, 15%, 18%, 20%, 22%, 25% depth of penetration compared to thickness of the fibrous media). In some embodiments, the portion of the fibrous media that is treated with the crosslinking agent may have complete penetration of the crosslinking agent into the fibrous media. In some embodiments, the crosslinking agent penetrates into the fibrous media at a depth of 1 mm to 5 mm (e.g., 1 mm, 2 mm, 3 mm, 4 mm, 5 mm). In some embodiments, the curled fiber mat can comprise curled fibers to a depth of 25% (e.g., 22%, 20%, 18%, 15%, 12%, 10%, 8%, 5%) or less, based on the thickness of the fiber mat. In some embodiments, the curled fiber mat can comprise curled fibers to a depth of 1 mm to 5 mm (e.g., 1 mm, 2 mm, 3 mm, 4 mm, 5 mm), based on the thickness of the fiber mat.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

In all of the Examples below, the rewet and acquisition time of the tested media were measured according to the MA003-1 method available at www.diapersworldwide.com, summarized below.
1. Prepare the desired wetting liquid (e.g. 0.9% saline) and add a small amount of dye to aid in visualization.
2. Weigh the diapers to be tested.
3. Weigh 20, 30, and 40 g stacks of Whatman filter paper to the nearest 0.01 g and record the weight of each stack as the dry filter paper weight.
4. Find and mark the dosing zone on the diaper. The dosing zone is located 5 cm toward the front edge of the product, from the center (diaper chassis, not core).
5. With the nonwoven coversheet side up, cup the diaper in a "U" shape.
6. Measure the desired amount (e.g., 80 ml) of the dyed wetting liquid (e.g., saline) and pour it into a separatory funnel.
Primary Acquisition/Rewet
7. Place a dosing ring (316.65 g total weight, 4.20 inches high, inside diameter 1.87 inches, outside diameter top 2.00 inches, outside diameter bottom 2.12 inches) and separatory funnel (with spigot 1 cm above product surface) over the dosing zone of the diaper and open the stopper. The dosing ring will sit on the surface of the diaper. Start the stopwatch as soon as the saline comes in contact with the surface of the diaper. Immediately after starting the stopwatch, start a ten-minute timer.
8. Stop the stopwatch once all of the wetting liquid has entered the diaper core and record this time (seconds) as the primary acquisition time.
9. Allow the article to swell for 10 minutes. Note: This ten-minute interval should start at the onset of the acquisition test, when the saline is first poured into the dosing ring.
10. After 10 minutes, place the 20 g stack of filter papers on the diaper (nonwoven coversheet side), centered on the marked dosing zone. Set a rewet weight (2.5 kg circular weight, 0.7 psi, 8 cm diameter) on top of the filter paper stack and keep it there for 2 minutes.
11. After 2 minutes, remove the weight and weigh the filter papers. Record the weight of the filter papers as the wet weight.
12. Subtract the dry weight of the first filter paper stack from the wet weight of the first filter paper stack and record the difference as the primary rewet.

Second Acquisition/Rewet
13. Repeat steps 6-9. The acquisition time measure in step 8 is the second acquisition time.
14. Repeat steps 10-12 using the 30 g stack of filter papers.
15. Subtract the dry weight of the second filter paper stack from the wet weight of the second filter paper stack and record the difference as the second rewet.
Third Acquisition/Rewet
16. Repeat steps 6-9. The acquisition time measure in step 8 is the second acquisition time.
14. Repeat steps 10-12 using the 40 g stack of filter papers.
15. Subtract the dry weight of the third filter paper stack from the wet weight of the third filter paper stack and record the difference as the third rewet.
Calculation Rewet value (g) = wet weight of filter papers (g) − dry weight of filter papers (g)

The acquisition time is measured in seconds and is reported to the nearest 0.1 sec.

Example 1: Acquisition and Distribution Layer (ADL) Media

Four parts of Southern Bleached Softwood Kraft pulp roll underwent a defibering process in a Kamas hammermill before being combined with one part of TREVIRA 255 bicomponent fibers (core-sheath PET/PE, 1.3 dtex, 6 mm). The blended fibers then underwent forming of a mat at a rate of 3.5 meters per minute on a Spike forming line. The mat was consolidated in a through-air oven at 185° C. for 69 seconds. The mat was then sprayed on top side with a solution of citric acid and sodium hypophosphite monohydrate in the ratio of 1:0.3 at an add on of 5% weight dry over media weight. The solution was applied to the fibrous media using a laboratory spraying system consisting of four flat spray nozzles with a spray angle of 40° and an approximate orifice diameter of 0.026 inch. The nozzles were fixed to a spray boom placed 25 cm above a conveyor belt carrying the fibrous media and moving at a speed of 4 m/min. Distance between neighboring nozzles on the boom was set to 16.5 cm. The solution was sprayed onto the media at a flow rate of 1.5 L/min. The media was then dried and subsequently cured at 180 degrees C. for 5 minutes. The finished basis weight of the media was 116 gsm.

Figure 2:
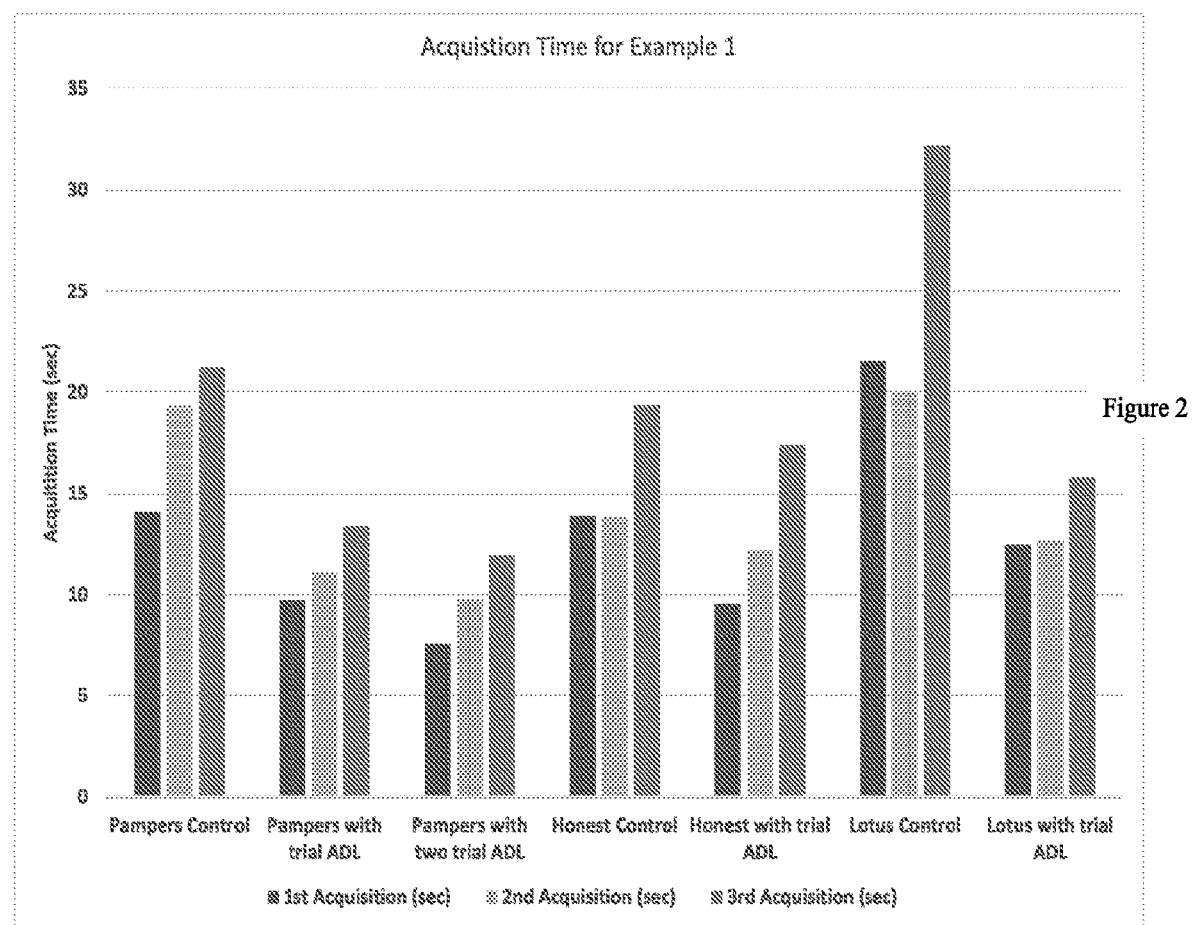
FIG. 2 shows acquisition times for commercial diapers with their normal absorption-distribution layers (ADL) (control) and the commercial diapers with trial ADL replacing the control ADL.
Figure 3:
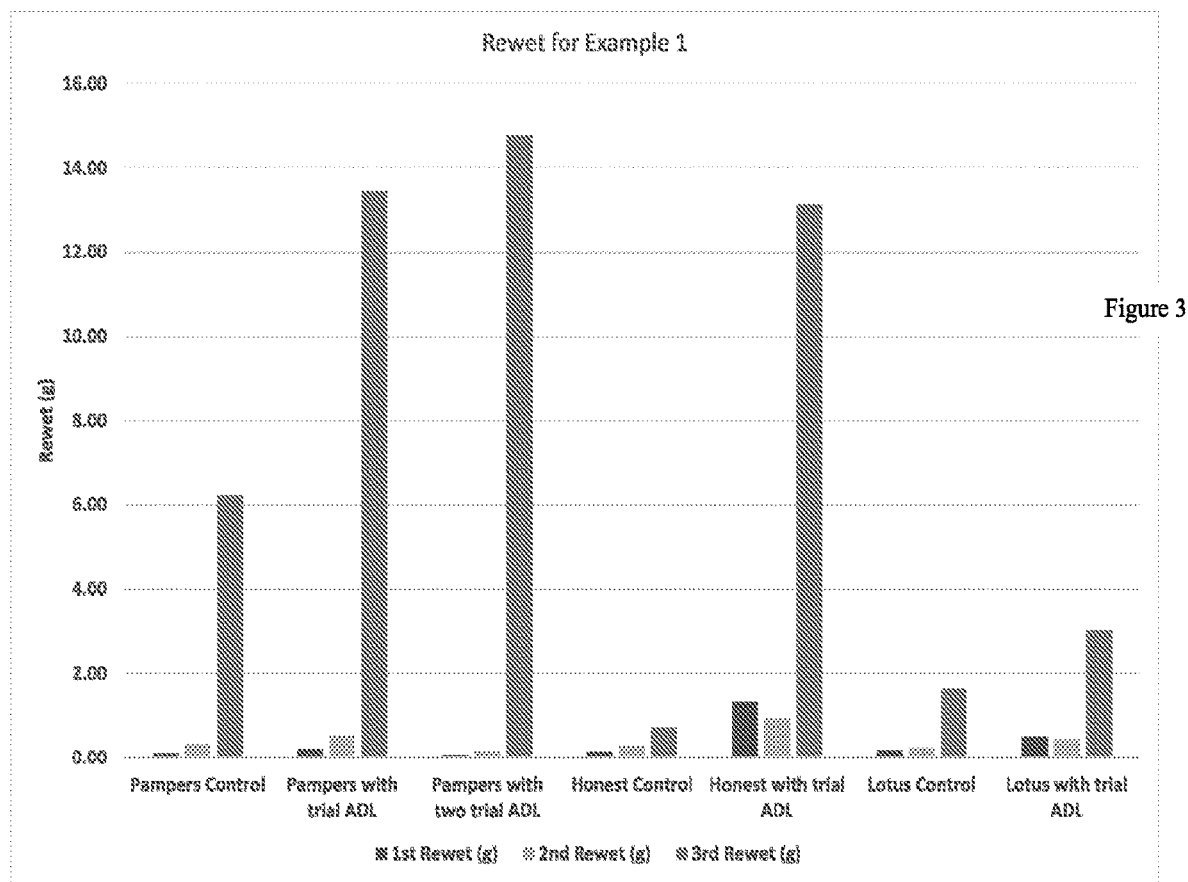
FIG. 3 shows rewet results for commercial diapers with their normal absorption-distribution layers (ADL) (control) and the commercial diapers with trial ADL replacing the control ADL.

The samples were tested by carefully removing the acquisition and distribution layer (ADL) from a commercial diaper and replacing it with the trial ADL. In the control sample, the same ADL was put back into the diaper. The acquisition and rewet conditions were: 80 mL insults of 0.9% saline solution at 10-minute intervals, using the acquisition and rewet method described above. The flow rate used was 7 mL/sec. The rewet was measured after pressing the absorbent pad onto the diaper at a pressure of 0.7 psi. The properties of the finished media for application as an acquisition and distribution layer are shown in Table 1 and FIGS. 2 and 3.

TABLE 1

| Sample | Weight Before Test (g) | Weight After Test (g) | 1st Acquisition (sec) | 2nd Acquisition (sec) | 3rd Acquisition (sec) | 1st Rewet (g) | 2nd Rewet (g) | 3rd Rewet (g) |
|---|---|---|---|---|---|---|---|---|
| Pampers Control | 32.4 | 261.7 | 14.06 | 19.31 | 21.24 | 0.10 | 0.31 | 6.22 |
| Pampers with trial ADL | 30.5 | 251.8 | 9.72 | 11.07 | 13.38 | 0.21 | 0.52 | 13.44 |
| Pampers with two trial ADL | 33.5 | 252.5 | 7.55 | 9.76 | 11.92 | 0.06 | 0.16 | 14.78 |
| Honest Control | 38.9 | 273.1 | 13.89 | 13.85 | 19.32 | 0.15 | 0.26 | 0.72 |
| Honest with trial ADL | 39.3 | 262.0 | 9.54 | 12.19 | 17.38 | 1.32 | 0.95 | 13.13 |
| Lotus Control | 36.4 | 269.2 | 21.52 | 19.94 | 32.19 | 0.17 | 0.24 | 1.64 |
| Lotus with trial ADL | 35.4 | 271.2 | 12.45 | 12.64 | 15.76 | 0.49 | 0.44 | 3.01 |

The trial ADL improved acquisition times in all three commercial diapers. The first and second rewets with the trial ADL were comparable to one another, but slightly higher than the first and second rewets relative to the control ADL. However, the third rewet was high for the trial ADL relative to the control ADL.

Example 2: Evaluation of Different Chemical Treatments

Four parts of Southern Bleached Softwood Kraft pulp roll underwent a defibering process in a Kamas hammermill before being combined with one part of TREVIRA 255 bicomponent fibers (core-sheath PET/PE, 1.3 dtex, 6 mm). The blended fibers then underwent forming of a mat at a rate of 3.5 meters per minute on a Spike forming line. The mat was consolidated in a through-air oven at 185° C. for 69 seconds.

Figure 4:
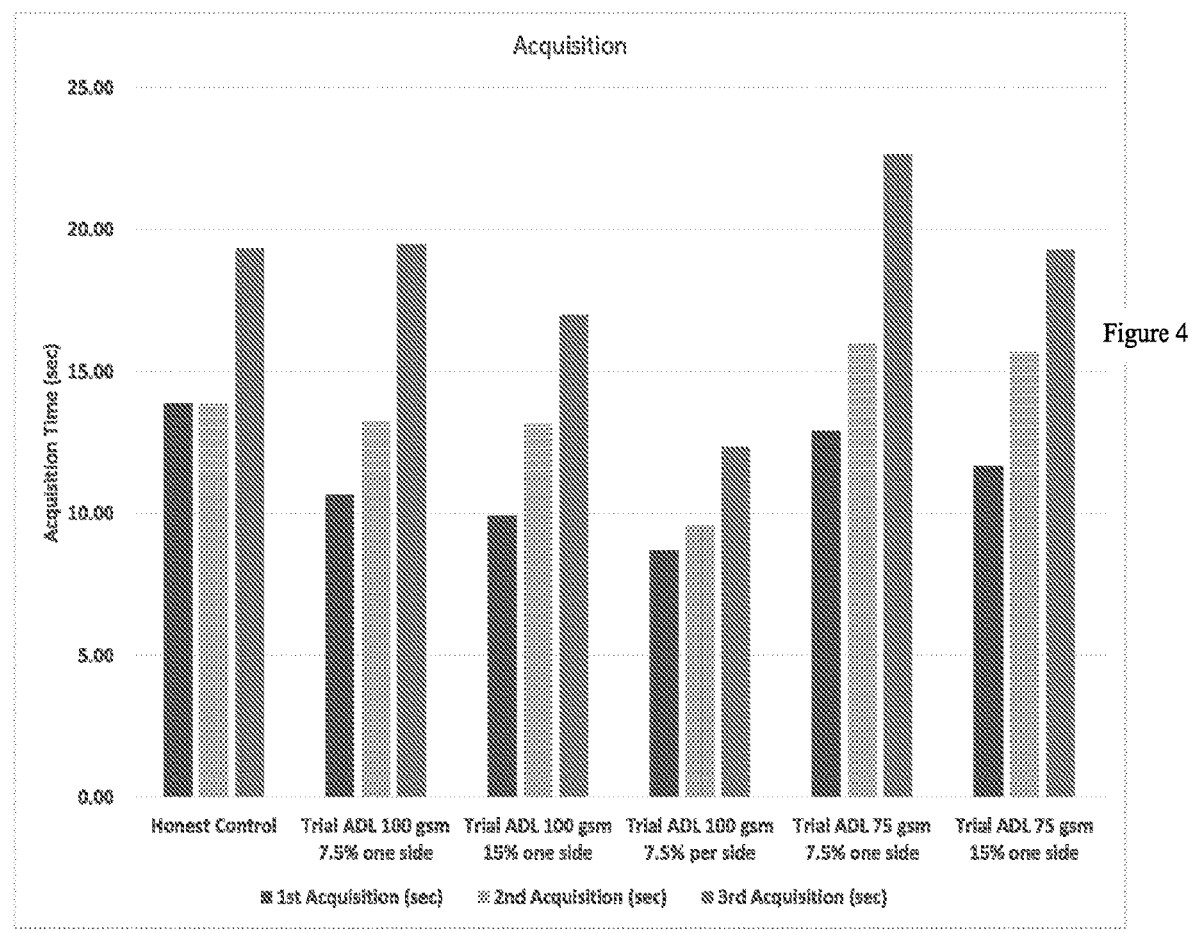
FIG. 4 shows acquisition times for trial ADL with different chemical treatments and amounts of the treatments.
Figure 5:
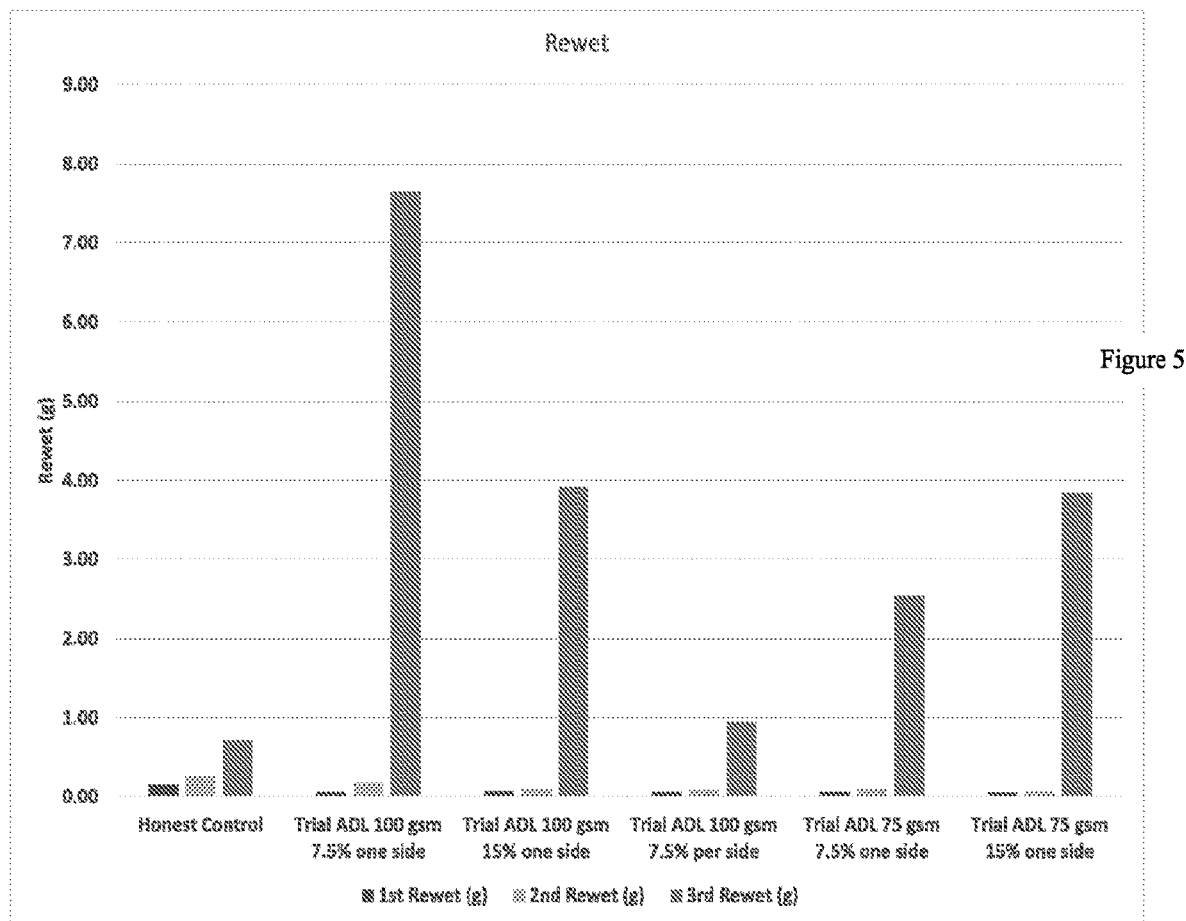
FIG. 5 shows rewet results for trial ADL with different chemical treatments and amounts of the treatments.

The mat was then sprayed on top side with a solution of citric acid and sodium hypophosphite monohydrate in the ratio of 1:0.3 at an add on of 7.5% total dry weight over dry weight. The solution was applied to the fibrous media using a laboratory spraying system consisting of four flat spray nozzles with a spray angle of 40° and an approximate orifice diameter of 0.026 inch. The nozzles were fixed to a spray boom placed 25 cm above a conveyor belt carrying the fibrous media and moving at a speed of 4 m/min. Distance between neighboring nozzles on the boom was set to 16.5 cm. The solution was sprayed onto the media at a flow rate of 1.5 L/min. The media was then dried and subsequently cured at 180 degrees C. for 5 minutes. The finished basis weight of the media was 116 gsm. The add-on levels and sides treated are shown in Table 2 and FIGS. 4 and 5.

The samples were tested by carefully removing the acquisition and distribution layer (ADL) from a commercial diaper and replacing it with the trial ADL. In the control sample the same ADL was put back into the diaper. The acquisition and re-wet conditions were: 80 mL insults of 0.9% saline solution at 10-minute intervals. The flow rate used was 7 mL/sec. Rewet is measured after pressing the absorbent pad onto the diaper at a pressure of 0.7 psi. The properties of the finished media for application as an acquisition and distribution layer are shown in Table 2 and FIGS. 4 and 5.

The acquisition time was slightly improved by increasing the chemical dosage from 7.5% to 15% on the top side. Treating both sides of the media showed the lowest acquisition times as in FIG. 4. Increasing the chemical treatment from 7.5% to 15% still showed high third rewets. However, treating the media on both sides with 7.5% of the solution significantly improved the third rewet and produced results similar to the commercial sample, see FIGS. 4 and 5.

TABLE 2

Results for different chemical treatments on the media

| Sample | Weight Before Test (g) | Weight After Test (g) | 1st Acquisition (sec) | 2nd Acquisition (sec) | 3rd Acquisition (sec) | 1st Rewet (g) | 2nd Rewet (g) | 3rd Rewet (g) |
|---|---|---|---|---|---|---|---|---|
| Honest Control | 38.9 | 273.1 | 13.89 | 13.85 | 19.32 | 0.15 | 0.26 | 0.72 |
| Trial ADL 100 gsm 7.5% one side | 37.4 | 267.7 | 10.68 | 13.27 | 19.48 | 0.06 | 0.17 | 7.65 |
| Trial ADL 100 gsm 15% one side | 38.0 | 272.3 | 9.93 | 13.18 | 17.00 | 0.07 | 0.09 | 3.92 |
| Trial ADL 100 gsm 7.5% per side | 41.0 | 278.4 | 8.70 | 9.57 | 12.35 | 0.06 | 0.08 | 0.95 |

TABLE 2-continued

Results for different chemical treatments on the media

| Sample | Weight Before Test (g) | Weight After Test (g) | 1st Acquisition (sec) | 2nd Acquisition (sec) | 3rd Acquisition (sec) | 1st Rewet (g) | 2nd Rewet (g) | 3rd Rewet (g) |
|---|---|---|---|---|---|---|---|---|
| Trial ADL 75 gsm 7.5% one side | 38.7 | 274.2 | 12.94 | 16.02 | 22.65 | 0.06 | 0.09 | 2.54 |
| Trial ADL 75 gsm 15% one side | 37.5 | 272.0 | 11.68 | 15.70 | 19.30 | 0.05 | 0.07 | 3.83 |

Example 3: Evaluation of Compression of Media and Basis Weight Reduction

Four parts of Southern Bleached Softwood Kraft pulp roll underwent a defibering process in a Kamas hammermill before being combined with one part of TREVIRA 255 bicomponent fibers (core-sheath PET/PE, 1.3 dtex, 6 mm). The blended fibers then underwent forming on a Danweb drum former at a rate of approximately 4 m/min. The media was consolidated in a through-air bicomponent (bico) bonding oven at 185° C. for 69 seconds. The compressed samples were produced by compacting the airlaid media after the forming head and before consolidation in the through air bico bonding oven. The caliper was reduced by approximately 35%. The media were then sprayed with dosages of a solution of citric acid and sodium hypophosphite monohydrate in the ratio of 1:0.3. The add-on levels and sides treated are shown in Table 3. The samples were first sprayed on the top side and dried using the same bico bonding oven described above. The roll was flipped and the second side of the media was sprayed and dried as above. The solution was applied to the fibrous media using a spraying system installed on the Danweb line. That system consisted of four flat spray nozzles (UniJet, type TP, orifice number 730039) fixed to a spray boom such that the opening of the nozzles was located 20 cm above the conveyor belt. Nozzle pressure and flow rate were adjusted until the total amount of solution added to the fibrous media was about 425 g/m2.

Figure 6:
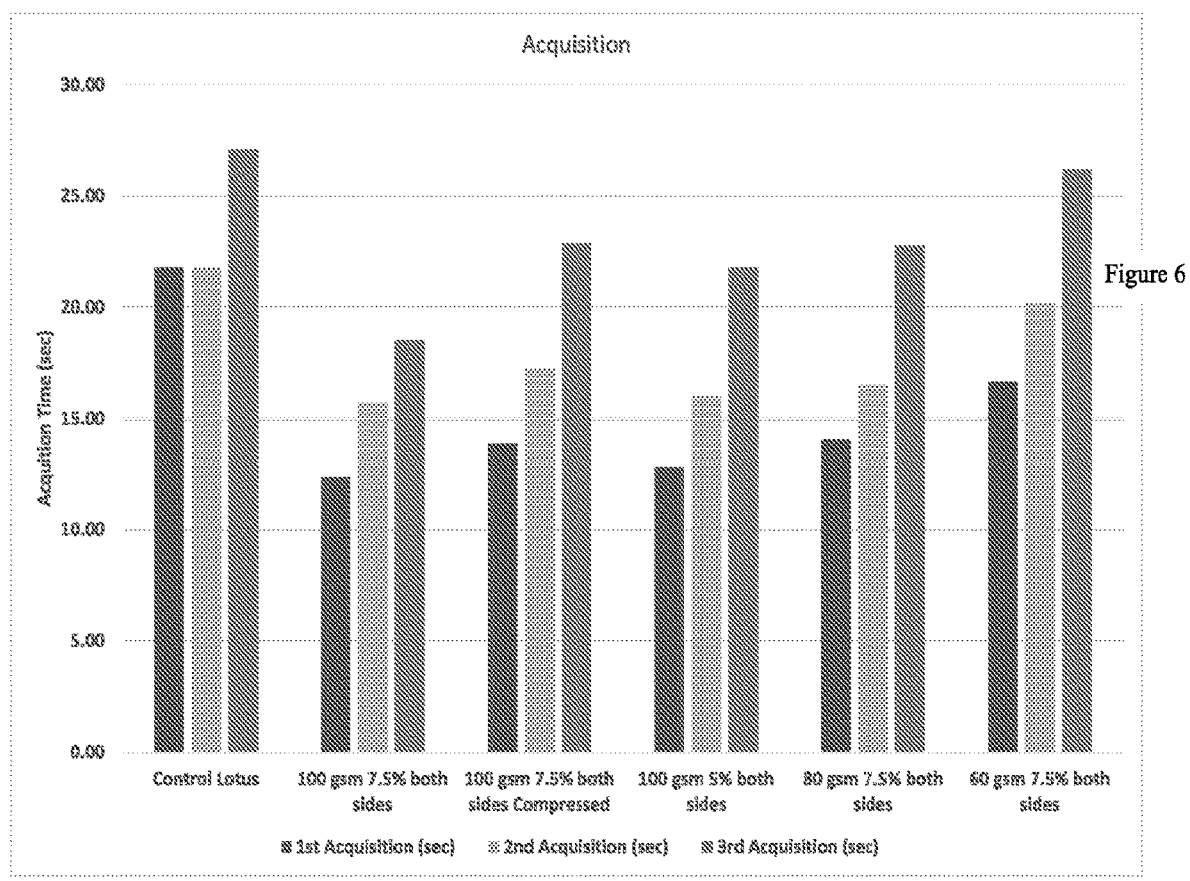
FIG. 6 shows acquisition times for trial ADL made from compressed and/or lighter weight media.
Figure 7:
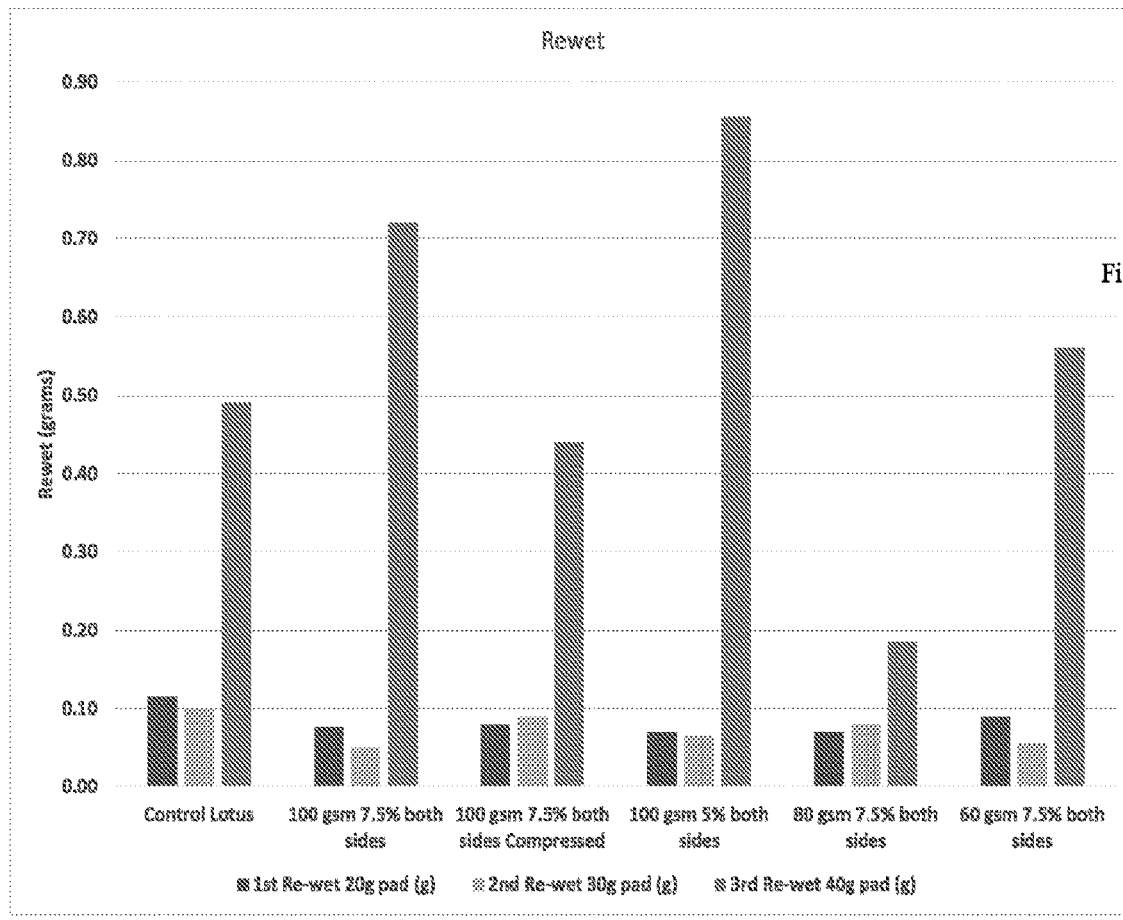
FIG. 7 shows rewet results for trial ADL made from compressed and/or lighter weight media.

The samples were tested by carefully removing the acquisition and distribution layer (ADL) from a commercial diaper and replacing it with the trial ADL. In the control sample the same commercial ADL was put back into the diaper. The acquisition and rewet conditions were: 80 mL insults of 0.9% saline solution at 10-minute intervals, using the acquisition and rewet method described above. The flow rate used was 7 mL/sec. Rewet was measured after pressing the absorbent pad onto the diaper at a pressure of 0.7 psi. The properties of the finished media for application as an acquisition and distribution layer are shown in Table 3 and FIGS. 6 and 7.

All of the media tested showed improved acquisition over the commercial control. As the basis weight was reduced, the acquisition time trended higher. The same trend was observed for compressing the media and reducing the dosage of the treatment, shown in FIGS. 6 and 7.

The rewet results of the various trial media were similar to the commercial sample tested. Reducing the basis weight improved the third rewet, while reducing the chemical treatment dosage negatively impacted the third rewet. Compressing the media improved the third rewet.

TABLE 3

Acquisition and rewet results for different basis weight medias and effect of reduced caliper on media.

| Sample | Diaper Before testing (8) | Diaper After testing (8) | 1st Acquisition (sec) | 2nd Acquisition (sec) | 3rd Acquisition (sec) | 1st Rewet 20 g pad (g) | 2nd Rewet 30 g pad (g) | 3rd Rewet 40 g pad (g) |
|---|---|---|---|---|---|---|---|---|
| Control Lotus | 35.2 | 271.8 | 21.79 | 21.77 | 27.13 | 0.12 | 0.10 | 0.49 |
| 100 gsm 7.5% both sides | 37.5 | 274.1 | 12.33 | 15.73 | 18.52 | 0.08 | 0.05 | 0.72 |
| 100 gsm 7.5% both sides Compressed | 37.4 | 274.2 | 13.89 | 17.22 | 22.87 | 0.08 | 0.09 | 0.44 |
| 100 gsm 5% both sides | 37.3 | 272.9 | 12.77 | 16.02 | 21.76 | 0.07 | 0.07 | 0.86 |
| 80 gsm 7.5% both sides | 35.9 | 273.8 | 14.07 | 16.51 | 22.76 | 0.07 | 0.08 | 0.19 |
| 60 gsm 7.5% both sides | 36.2 | 272.0 | 16.66 | 20.18 | 26.21 | 0.09 | 0.06 | 0.56 |

Example 4: Curl and Fiber Measurements

Samples of media described in Example 1 were redispersed using TAPPI/ANSI 205 sp-18. These fiber dispersions were then tested for curl, fiber length and kink with a Fiber Quality Analyzer using method TAPP/ANSI T 271 om-18. The results in Table 4 show the increase in curl index as a function of the treatment and curing.

TABLE 4

Fiber quality measurements as a function of chemical treatment and curing

| | Curl Index | Fiber Length (Lw) | Kink |
|---|---|---|---|
| Fibrous Media | 0.189 | 2.095 | 0.93 |
| Fibrous Media Treated and Dried | 0.229 | 2.116 | 1.06 |
| Fibrous Media Treated, Dried and Cured (5 min at 180 C.) | 0.311 | 1.917 | 1.27 |

The following non-exhaustive list of items is disclosed herein.

Item 1. A method comprising:
  forming a fibrous media from a fibrous material,
  treating the fibrous media with a crosslinking agent to form a treated fibrous media, and
  drying and/or curing the treated fibrous media to produce a curled fiber mat.

Item 2. The method of item 1, wherein the fibrous material comprises a cellulosic pulp fiber.

Item 3. The method of item 1 or item 2, wherein the fibrous material comprises Kraft pulp.

Item 4. The method of any of items 1-3, wherein the drying is at a temperature of 100° C. or greater.

Item 5. The method of any of items 1-4, wherein the drying is for a time from 10 seconds to 10 minutes.

Item 6. The method of any of items 1-5, wherein the curing is at a temperature of 145° C. or greater.

Item 7. The method of any of items 1-6, wherein the curing is at a temperature of 180° C. to 190° C.

Item 8. The method of any of items 1-7, wherein the curing is for a time from 30 seconds or greater.

Item 9. The method of any of items 1-8, wherein the curing is for a time from 30 seconds to 5 minutes.

Item 10. The method of any of items 1-9, wherein the drying occurs before and separate from the curing.

Item 11. The method of any of claims 1-10, wherein the curing and the drying occur simultaneously.

Item 12. The method of any of items 1-11, wherein the crosslinking agent comprises a carboxylic acid.

Item 13. The method of any of items 1-12, wherein the crosslinking agent is selected from the group consisting of citric acid, glutaraldehyde, and combinations thereof.

Item 14. The method of any of items 1-13, wherein the crosslinking agent is present in an amount of 5% to 20%, based on the weight of the fibrous material.

Item 15. The method of any of items 1-14, wherein the crosslinking agent comprises:
  3.5% to 5% citric acid, by weight of the fibrous material, and
  1% to 2.5% glutaraldehyde, by weight of the fibrous material.

Item 16. The method of any of items 1-15, further comprising a hypophosphite.

Item 17. The method of any of items 1-16, further comprising a bonding material (e.g., a bonding fiber, a liquid binder, and combinations thereof).

Item 18. The method of any of items 1-17, further comprising an additive.

Item 19. The method of any of items 1-18, wherein the curled fiber mat has a final curl index of 0.28 or greater.

Item 20. The method of any of items 1-18, wherein the curled fiber mat has a final curl index of 0.32 or greater.

Item 21. The method of any of items 1-20, wherein the curled fiber mat has a thickness of 0.5 mm to 3 mm.

Item 22. The method of any of items 1-20, wherein the curled fiber mat has a thickness of 8 mm to 12 mm.

Item 23. A product made by the method according to any one of items 1-22.

Item 24. The product of item 23, wherein the product is an acquisition and distribution layer.

Item 25. The product of item 23, wherein the product comprises an acquisition and distribution layer.

Item 26. The product of item 23, wherein the product comprises an acquisition and distribution layer and absorbent core.

Item 27. The product of item 23, wherein the curled fiber mat comprises an integral acquisition and distribution layer and absorbent core.

Item 28. The product of any of items 23-27, wherein the curled fiber mat comprises curled fibers to a depth of 25% or less of the thickness of the curled fiber mat.

Item 29. The product of any of items 23-27, wherein the curled fiber mat comprises curled fibers to a depth of 10% or less of the thickness of the curled fiber mat.

Item 30. The method of any of items 1-22, wherein the fibrous media is produced by an airlaid process or a wetlaid process.

Item 31. The method of any of items 1-22, wherein the curled fiber mat is a curled fiber airlaid mat or a curled fiber wetlaid mat.

Item 32. The product of item 23, wherein the product comprises a curled fiber airlaid mat or a curled fiber wetlaid mat.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily utilized as a basis for the design of other structures, methods, and systems for carrying out the several purposes of the embodiments and claims presented in this application. It is important, therefore, that the claims be regarded as including such equivalent constructions.

I claim:

1. A method comprising:
  forming not previously curled fiber mat comprising bicomponent fibers and not previously curled cellulosic pulp fibers,
  treating the not previously curled fiber mat with a crosslinking agent to form a treated not previously curled fiber mat, and
  drying and/or curing the treated not previously curled fiber mat to produce a curled fiber mat,
  wherein the step of drying and/or curing the treated fiber mat produces curled cellulosic fibers,
  wherein the curled cellulosic fibers are crosslinked internally by the crosslinking agent to form permanently curled cellulosic fibers, and wherein the curled fiber mat comprises bicomponent fibers that are bonded with the permanently curled cellulosic pulp fibers.

2. The method of claim 1, wherein the drying is at a temperature of 100°0 C. or greater.

3. The method of claim 1, wherein the drying is for a time from 10 seconds to 10 minutes.

4. The method of claim 1, wherein the curing is at a temperature of 145° C. or greater.

5. The method of claim 1, wherein the curing is at a temperature of 180° C. to 190° C.

6. The method of claim 1, wherein the curing is for a time from 30 seconds or greater.

7. The method of claim 1, wherein the curing is for a time from 30 seconds to 5 minutes.

8. The method of claim 1, wherein the drying occurs before and separate from the curing.

9. The method of claim 1, wherein the curing and the drying occur simultaneously.

10. The method of claim 1, wherein the crosslinking agent comprises a carboxylic acid.

11. The method of claim 1, wherein the crosslinking agent is selected from the group consisting of citric acid, glutaraldehyde, and combinations thereof.

12. The method of claim 1, wherein the crosslinking agent is present in an amount of 3.5% to 20%, based on the weight of the not previously curled fiber mat.

13. The method of claim 1, wherein the crosslinking agent comprises citric acid and a hypophosphite.

14. The method of claim 13, wherein the citric acid is added in an amount of at least 0.5% by weight, based on the weight of the not previously curled fiber mat, and
wherein the citric acid and the hypophosphite are in a ratio of 1 citric acid to 0.2-0.4 hypophosphite based on the weight of the not previously curled fiber mat.

15. The method of claim 1, wherein the curled fiber mat has a final curl index of 0.28 or greater.

16. The method of claim 1, wherein the curled fiber mat has a thickness of 0.5 mm to 3 mm.

17. The method of claim 1, wherein the curled fiber mat is a curled fiber airlaid mat or a curled fiber wetlaid mat.

18. The method of claim 1, wherein the not previously curled fiber mat is made by an airlaid process or a wetlaid process.

19. The method of claim 1, wherein the not previously curled cellulosic pulp fibers comprise not previously curled Kraft pulp fibers.

* * * * *